(12) United States Patent
Karunasiri et al.

(10) Patent No.: US 11,973,354 B2
(45) Date of Patent: Apr. 30, 2024

(54) SYSTEMS AND METHODS FOR WIRELESSLY TRANSMITTING POWER AND DATA TO AN IMPLANTABLE STIMULATOR

(71) Applicant: Advanced Bionics AG, Staefa (CH)

(72) Inventors: R. Tissa Karunasiri, Valencia, CA (US); Glen A. Griffith, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 316 days.

(21) Appl. No.: 17/566,870

(22) Filed: Dec. 31, 2021

(65) Prior Publication Data

US 2022/0123603 A1 Apr. 21, 2022

Related U.S. Application Data

(63) Continuation of application No. 17/107,276, filed on Nov. 30, 2020, now Pat. No. 11,251,660, which is a
(Continued)

(51) Int. Cl.
*H04R 25/00* (2006.01)
*A61N 1/36* (2006.01)
(Continued)

(52) U.S. Cl.
CPC .......... *H02J 50/80* (2016.02); *A61N 1/36038* (2017.08); *A61N 1/37252* (2013.01);
(Continued)

(58) Field of Classification Search
CPC .. H04R 25/552; H04R 25/554; H04R 25/558; H04S 2400/01; H04S 2420/01; H04S 5/00
See application file for complete search history.

(56) References Cited

U.S. PATENT DOCUMENTS 5,991,664 A 11/1999 Seligman
10,646,164 B1 5/2020 Perryman et al.
(Continued)

FOREIGN PATENT DOCUMENTS

EP 2376185 10/2011
WO 2010056768 5/2010

OTHER PUBLICATIONS

"International Search Report and Written Opinion in corresponding International Application No. PCT/US2021/059236, dated Feb. 28, 2022".
(Continued)

*Primary Examiner* — Amir H Etesam
(74) *Attorney, Agent, or Firm* — ALG Intellectual Property, LLC

(57) ABSTRACT

A system includes electronic circuitry that receives a self-clocking differential signal comprising a data signal encoded with a clock signal at a dock frequency. The electronic circuitry is configured to recover, from the self-docking differential signal, the data signal and the dock signal. Then, based on the recovered dock signal, the electronic circuitry is configured to wirelessly transmit, to an implantable stimulator implanted within a recipient, a forward telemetry signal representing data recovered from the data signal. Corresponding systems, methods, devices, and application specific integrated circuits (ASICs) are also disclosed.

20 Claims, 13 Drawing Sheets

Related U.S. Application Data continuation-in-part of application No. PCT/US2019/051426, filed on Sep. 17, 2019, and a continuation-in-part of application No. 16/536,760, filed on Aug. 9, 2019, now Pat. No. 11,121,586, which is a continuation of application No. 15/995,099, filed on May 31, 2018, now Pat. No. 10,418,862.

(51) Int. Cl.
| | | |
|---|---|---|
| A61N 1/372 | (2006.01) | |
| A61N 1/378 | (2006.01) | |
| G01R 23/02 | (2006.01) | |
| G06F 1/04 | (2006.01) | |
| H01Q 1/24 | (2006.01) | |
| H02J 50/27 | (2016.01) | |
| H02J 50/80 | (2016.01) | |
| H04R 1/10 | (2006.01) | |
| A61F 2/18 | (2006.01) | |
| A61N 1/02 | (2006.01) | |

(52) U.S. Cl.
CPC ........... *A61N 1/3787* (2013.01); *G01R 23/02* (2013.01); *G06F 1/04* (2013.01); *H01Q 1/248* (2013.01); *H02J 50/27* (2016.02); *H04R 1/1025* (2013.01); *H04R 25/70* (2013.01); *A61F 2/18* (2013.01); *A61F 2002/183* (2013.01); *A61N 1/025* (2013.01); *A61N 1/3727* (2013.01)

(56) References Cited

U.S. PATENT DOCUMENTS

| | | |
|---|---|---|
| 2005/0251225 A1 | 11/2005 | Faltys |
| 2006/0190059 A1 | 8/2006 | Griffith |
| 2011/0009924 A1 | 1/2011 | Meskens |
| 2011/0150255 A1 | 6/2011 | Solum |
| 2011/0208329 A1 | 8/2011 | Castor-Perry |
| 2014/0240604 A1 | 8/2014 | Toba et al. |
| 2015/0352359 A1 | 12/2015 | Fredelake |
| 2016/0375243 A1 | 12/2016 | Roehrlein et al. |
| 2017/0028199 A1 | 2/2017 | Roehrlein et al. |
| 2017/0189694 A1* | 7/2017 | Palmer ............... A61N 1/36038 |
| 2017/0244495 A1 | 8/2017 | Ouzounov |
| 2017/0246462 A1 | 8/2017 | Meskens |
| 2018/0050198 A1 | 2/2018 | Mazanec |
| 2019/0372405 A1 | 12/2019 | Karunasiri |

OTHER PUBLICATIONS

Asgarian, et al., "A Low-Power Noncoherent BPSK Demodulator and Clock Recovery Circuit for High-Data-Rate Biomedical Applications", 31st Annual Conference of the IEEE EMBS, Sep. 3, 2009.
"International Search Report and Written Opinion received in International Application No. PCT/US2019/034596, dated Oct. 24, 2019."
"International Search Report and Written Opinion received in International Application No. PCT/US2019/051426."
Garcerán-Hernández, et al., "Cochlear implant: Transcutaneous transmission link with OFDM", Jun. 10, 2013, Natural and Artificial Models in Computation and Biology, Springer Berlin Heidelberg, Berlin. pp. 358-367, XP047030847. ISBN: 978-3-642-38636-7; pp. 358-363; figure 1.

* cited by examiner

SYSTEMS AND METHODS FOR WIRELESSLY TRANSMITTING POWER AND DATA TO AN IMPLANTABLE STIMULATOR

RELATED APPLICATIONS

The present application is a continuation of U.S. patent application Ser. No. 17/107,276, filed Nov. 30, 2020, which is a continuation-in-part of U.S. patent application Ser. No. 16/536,760, filed Aug. 9, 2019 and issued as U.S. Pat. No. 11,121,586, which is a continuation application of U.S. patent application Ser. No. 15/995,099, filed May 31, 2018 and issued as U.S. Pat. No. 10,418,862. U.S. patent application Ser. No. 17/107,276 is also a continuation-in-part of PCT International Application No. PCT/US2019/051426, filed Sep. 17, 2019. The contents of all of these applications are hereby incorporated by reference in their respective entireties.

BACKGROUND INFORMATION

Various types of implantable stimulation systems used to treat various medical conditions may be configured, when implanted within a recipient's body, to operate based on power and/or data received from outside the recipient's body. For example, conventional cochlear implant systems may include an external sound processor that provides power and data to an implanted cochlear implant by way of a passive headpiece communicatively coupled with the cochlear implant. In some examples, for instance, the sound processor may be worn behind an ear of a recipient and may include components such as a battery, a microphone, sound processing circuitry, and wireless transmission circuitry. The sound processor may transmit data-modulated AC power through the skin of the recipient to the cochlear implant by way of an antenna coil embedded within a headpiece that is separate from and connected by way of a cable to the sound processor (e.g., a headpiece that is attached to the head at a location that is more closely aligned with the cochlear implant). Other types of implantable stimulation systems (e.g., neurostimulation systems, spinal cord stimulation systems, cardiac stimulation systems, etc.) may operate in similar ways.

Unfortunately, there may be certain drawbacks to transmitting power and data from an external device producing the power and data (e.g., the sound processor in the cochlear implant system example) to a passive transmission device (e.g., the passive headpiece in the cochlear implant system example). For instance, unwanted emissions emanating from a cable between the external device producing the power and data and the passive transmission device may cause emission compliance issues and/or may be a source of inefficiency compromising the battery life of the implantable stimulation system. Additionally, this conventional power and data transmission paradigm may not be particularly flexible. For example, in order for an external device to function properly with a given implanted stimulator device (e.g., a previously-implanted stimulator device such as a legacy cochlear implant in one example), the external device must be capable of providing power and/or data at one or more particular carrier frequencies with which the implanted stimulator device is compatible. Such requirements may place undesirable constraints on the design of the external device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
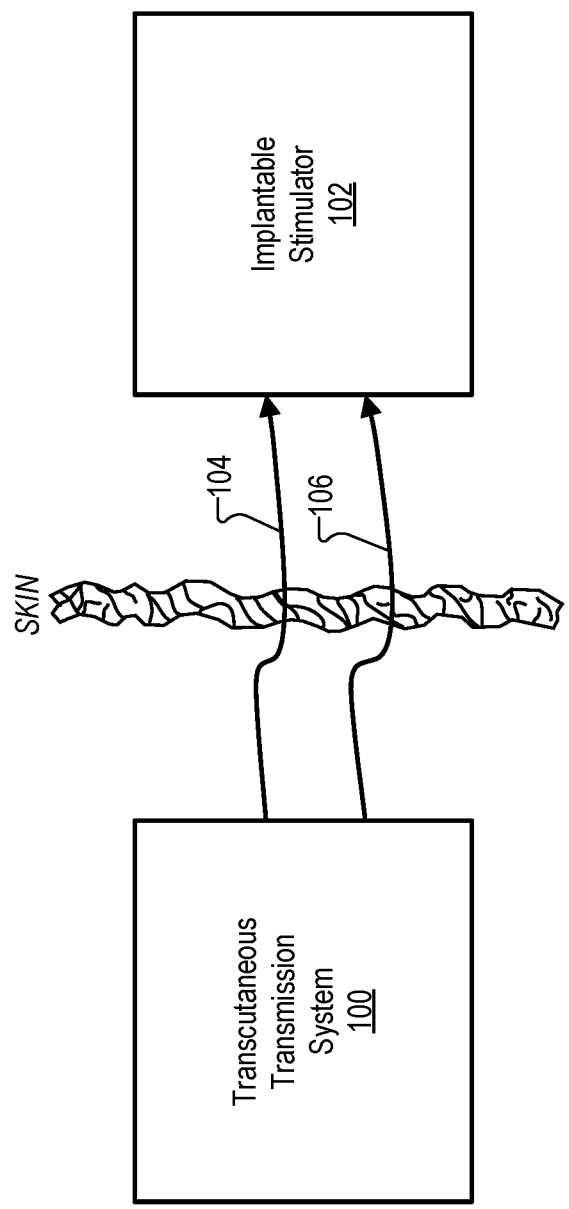
FIG. 1 shows an illustrative transcutaneous transmission system configured to wirelessly transmit power and data to an implantable stimulator according to principles described herein.

Systems and methods for wirelessly transmitting power and data to an implantable stimulator are described herein. Conventional passive transmission devices of conventional implantable stimulation systems (e.g., passive headpieces of conventional cochlear implant systems, etc.) may include a passive coil antenna and a network of passive components (e.g., capacitors, inductors, transformers, etc.). In contrast, as will be described in more detail below, transcutaneous transmission systems described herein (e.g., including active headpieces of cochlear implant systems), may serve within implantable stimulation system as transmission devices that further include active (i.e., powered) components and circuitry as may serve a particular implementation.

For example, an illustrative transcutaneous transmission system included within an implantable stimulation system (e.g., an active headpiece within a cochlear implant system) associated with a recipient may include a housing within which is disposed an interface assembly and active electronic circuitry (e.g., power supplies, logic chips, integrated circuits, wireless transmitters, etc.) configured to perform various operations using power received from an external device that produces power and data (e.g., a sound processor within a cochlear implant system). The housing of the transcutaneous transmission system may be configured to be located external to the recipient and may be separate from a housing of the external device producing the power and data and/or other such components of the implantable stimulation system. For example, in the case of a transcutaneous transmission system implemented as an active headpiece of a cochlear implant system, the housing of the active headpiece may be configured to be located on the recipient's head (e.g., held in place by a magnet) near an implantation site at which a cochlear implant is implanted within the recipient, while a sound processor implementing the external device may be worn behind the recipient's ear or otherwise carried on the recipient's body.

The interface assembly disposed within the housing of the transcutaneous transmission system may be communicatively coupled, by way of a cable, to the external device producing and providing power and data intended for an implantable stimulator implanted within the recipient. As such, the interface assembly may be configured to receive (e.g., from the external device by way of the cable) direct current ("DC") power and a self-clocking differential signal. The self-clocking differential signal may comprise a data signal encoded with a clock signal at a clock frequency. For example, the data signal may be representative of data configured for use by the implantable stimulator implanted within the recipient (e.g., a cochlear implant in the cochlear implant system example).

The electronic circuitry disposed within the housing of the transcutaneous transmission system may include any suitable active and/or passive circuitry configured to perform operations described herein. For example, the electronic circuitry may be configured to recover, from the self-clocking differential signal, the data signal and the clock signal at the clock frequency. Based on the recovered clock signal at the clock frequency, the electronic circuitry may generate one or more synthesized clock signals at one or more carrier frequencies. For example, the electronic circuitry may generate a single synthesized clock signal at a particular carrier frequency or may generate a first synthesized clock signal at a first carrier frequency (e.g., to be used for transmitting power) and a second synthesized clock signal at a second carrier frequency (e.g., to be used for transmitting data). In examples in which more than one synthesized clock frequency is generated, at least one of the carrier frequencies may be distinct from the clock frequency of the recovered clock signal. Using the one or more synthesized clock signals, the electronic circuitry may wirelessly transmit, to an implantable stimulator implanted within the recipient (e.g., wirelessly and transcutaneously through the skin of the recipient), both 1) alternating current ("AC") power based on the DC power, and 2) forward telemetry data based on the recovered data signal.

Systems and methods described herein for wirelessly transmitting power and data to an implantable stimulator may provide various benefits. For example, when AC power and data generated by components within the transcutaneous transmission system (as opposed to being generated by a separate external device connected to the transmission system by way of a cable) are transmitted directly from the transcutaneous transmission system to the implantable stimulator as described herein, efficiency may be increased and emissions decreased as compared to conventional configurations in which AC power and data are transmitted from the external device by way of a passive transmission device. Specifically, when AC power and data are generated at a separate external device such as a sound processor and transmitted by way of a cable (e.g., a coaxial cable) to be radiated by an antenna coil of a passive transmission device such as a passive headpiece, unwanted emissions may radiate out of the cable, causing power to be lost (i.e., thereby decreasing efficiency) and possibly creating issues for emission compliance requirements. These efficiency and emissions issues may be resolved by sending power and data to a transcutaneous transmission system (e.g., an active headpiece) such as the transcutaneous transmission systems described herein.

Additionally, by including clock generation circuitry and power and data transmission circuitry within a transcutaneous transmission system such as an active headpiece of a cochlear implant system (rather than in a separate external device such as the sound processor of the cochlear implant system), implantable stimulation system design may be streamlined to provide users with smaller and less bulky devices. A great degree of flexibility may also be provided by the systems and methods described herein. For example, because transcutaneous transmission systems described herein may recover clock signals at one frequency and then generate synthesized clock signals at other, different frequencies, various external devices and implantable stimulators may be able to operate compatibly with one another using the transcutaneous transmission systems where they may have been incompatible otherwise (e.g., due to clock frequencies, voltage levels, etc.). As will be described in more detail below, one or more AC signals (e.g., for power and/or data) may be exchanged between implantable stimulators and transcutaneous transmission systems disclosed herein at reconfigurable clock frequencies that may be conveniently set up and modified using software (e.g., by writing registers within the transcutaneous transmission system), rather than requiring updates to hardware.

Various specific embodiments will now be described in more detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. The disclosed systems and methods for wirelessly transmitting power and data to an implantable stimulator may provide any of the benefits mentioned above, as well as various additional and/or alternative benefits that will be described and/or made apparent below.

FIG. 1 shows an illustrative transcutaneous transmission system 100 ("system 100") configured to wirelessly transmit power and data to an illustrative implantable stimulator 102 in accordance with principles described herein. More particularly, FIG. 1 shows AC power 104 and forward telemetry data 106 that system 100 transmits wirelessly through the skin of a recipient to implantable stimulator 102. In FIG. 1, AC power 104 and forward telemetry data 106 are shown as two separate signals. As will be described in more detail below, system 100 may indeed send the power and data on two separate carrier signals in some implementations. For instance, AC power 104 may be transmitted on a first AC carrier signal having a first carrier frequency, while forward telemetry data 106 may be modulated (e.g., using an On-Off-Keying, Amplitude-Shift-Keying, or other suitable modulation technique) onto a second AC carrier signal having a second carrier frequency that may be the same or different from the first carrier frequency. In other implementations that will also be described and illustrated in more detail below, system 100 may wirelessly transmit the power and data on a single carrier signal. For example, an AC signal that carries AC power 104 at a particular carrier frequency may also be modulated with forward telemetry data 106.

System 100 may produce and wirelessly transmit AC power 104 and forward telemetry data to implantable stimulator 102 in any suitable way. For example, as will be described in more detail below, system 100 may include an interface assembly configured to receive DC power and a self-clocking differential signal comprising a data signal encoded with a clock signal at a clock frequency. The DC power and the self-clocking differential signal may be received from any suitable source such as another device that is external to the recipient's body and that generates the data signal and the clock signal using its own independent DC power source (e.g., a battery), clock generation circuitry (e.g., crystal oscillator, etc.), and so forth. As a result of receiving the DC power and the self-clocking differential signal from the external device in this way, system 100 may not necessarily need to include its own independent DC power source and/or clock generation circuitry. Omitting these components may be advantageous to the design of system 100, as will be described in more detail below. However, it will be understood that in certain implementations, system 100 may be designed to include its own independent power source (e.g., battery) and/or clock generation circuitry (e.g., crystal oscillator) as may serve a particular embodiment.

Along with the interface assembly for receiving the DC power and self-clocking differential signal, system 100 may further include electronic circuitry configured to perform various operations. For example, the electronic circuitry may recover the data signal and the clock signal from the self-clocking differential signal at the dock frequency, and, based on the recovered clock signal at the clock frequency, may generate a synthesized clock signal at a carrier frequency (e.g., a carrier frequency different from the clock frequency of the recovered clock signal). Using the synthesized clock signal, the electronic circuitry may then wirelessly transmit AC power 104 (based on the DC power) and forward telemetry data 106 (based on the recovered data signal) to implantable stimulator 102 as implantable stimulator 102 is implanted within the recipient. While the only communication explicitly illustrated between system 100 and implantable stimulator 102 is AC power 104 and forward telemetry data 106, it will be understood that other signals may further be transmitted between system 100 and implantable stimulator 102 in certain implementations. As one example that will be described in more detail below, implantable stimulator 102 may transmit backward telemetry data through the skin to system 100.

System 100 and implantable stimulator 102, as well as the external device mentioned above and/or other systems or devices involved in operations described herein, may be included as part of various types of implantable stimulation systems used for various purposes. For example, implantable stimulation systems that could implement a transcutaneous transmission system such as system 100 and an implantable stimulator such as implantable stimulator 102 include systems such as neurostimulation systems, spinal cord stimulation systems, cardiac stimulation systems, and various other types of implantable stimulation systems. To provide a more concrete implantable stimulation system example for purposes of illustration, a particular type of implantable stimulation system will now be described in detail. Specifically, the implantable stimulation system that will be the focus of the following disclosure is a cochlear implant system that includes: an active headpiece serving as system 100, a cochlear implant serving as implantable stimulator 102, a sound processor serving as the external device that generates the DC power and self-clocking differential signal based on its own independent power source and clock generation circuitry, and other components that will be described in more detail below. An example of a cochlear implant system will now be described, but it will be understood that the principles described with respect to the cochlear implant system may similarly apply to other types of implantable stimulation systems embodying other forms of transcutaneous transmission systems and implantable stimulators.

Figure 2:
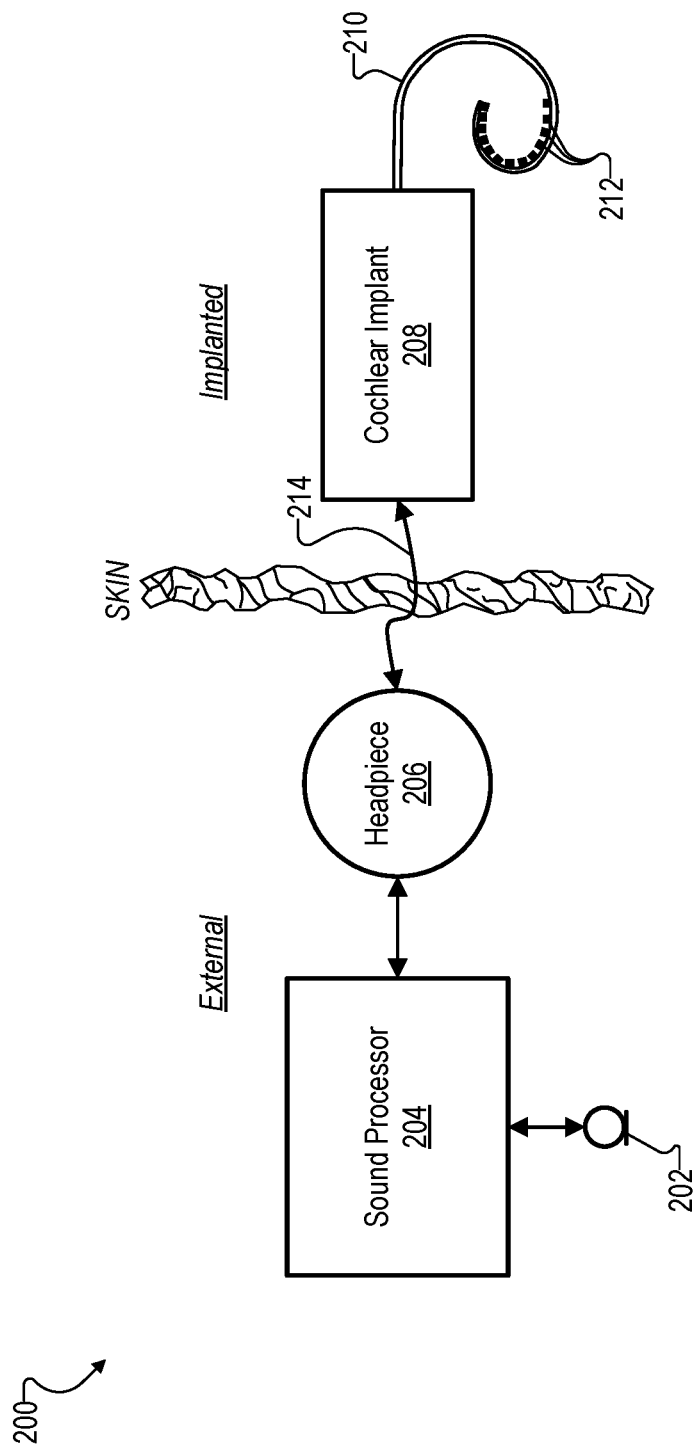
FIG. 2 shows an illustrative cochlear implant system implementing the transcutaneous transmission system and implantable stimulator of FIG. 1 according to principles described herein.

FIG. 2 shows an illustrative cochlear implant system 200 implementing system 100 and implantable stimulator 102 of FIG. 1. As shown, cochlear implant system 200 may include various components configured to be located external to a cochlear implant recipient (i.e., a user of the cochlear implant system) including, but not limited to, a microphone 202, a sound processor 204, and a headpiece 206. Cochlear implant system 200 may further include various components configured to be implanted within the recipient including, but not limited to, a cochlear implant 208 (also referred to as an implantable cochlear stimulator) and a lead 210 (also referred to as an intracochlear electrode array) with a plurality of electrodes 212 disposed thereon. As will be described in more detail below, additional or alternative components may be included within cochlear implant system 200 as may serve a particular implementation. The components shown in FIG. 2 will now be described in more detail.

Microphone 202 may be configured to detect audio signals presented to the recipient. Microphone 202 may be implemented in any suitable manner. For example, microphone 202 may include a microphone such as a T-MIC™ microphone from Advanced Bionics. Microphone 202 may be associated with a particular ear of the recipient such as by being located in a vicinity of the particular ear (e.g., within the concha of the ear near the entrance to the ear canal). In some examples, microphone 202 may be held within the concha of the ear near the entrance of the ear canal by a boom or stalk that is attached to an ear hook configured to be selectively attached to sound processor 204. Additionally or alternatively, microphone 202 may be implemented by one or more microphones disposed within sound processor 204, one or more microphones disposed within headpiece 206, and/or any other suitable microphone or microphones as may serve a particular implementation.

Sound processor 204 may be configured to direct cochlear implant 208 to generate and apply electrical stimulation (also referred to herein as "stimulation current") representative of one or more audio signals (e.g., one or more audio signals detected by microphone 202, input by way of an auxiliary audio input port, etc.) to one or more stimulation sites associated with an auditory pathway of the recipient such as an auditory nerve of the recipient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a recipient, it will be understood that stimulation current may also be applied to other suitable nuclei in the auditory pathway. To this end, sound processor 204 may process the one or more audio signals in accordance with a selected sound processing strategy or program to generate appropriate stimulation parameters for controlling cochlear implant 208. Sound processor 204 may include or be implemented by a behind-the-ear ("BTE") unit, a body worn device, and/or any other sound processing unit as may serve a particular implementation. In some examples, sound processor 204 may be implemented by an electroacoustic sound processor included in an electroacoustic hearing system configured to provide both electrical and acoustic stimulation to the recipient.

Sound processor 204 may wirelessly transmit power and/or stimulation parameters (e.g., in the form of data words included in a forward telemetry sequence) to cochlear implant 208 by way of a wireless communication link 214 between headpiece 206 and cochlear implant 208. It will be understood that communication link 214 may include a bidirectional communication link and/or one or more dedicated unidirectional communication links. In the same or other examples, sound processor 204 may transmit (e.g., wirelessly transmit) information such as an audio signal detected by microphone 202 to another sound processor (e.g., a sound processor associated with another ear of the recipient). For example, as will be described in more detail below, the information may be transmitted to the other sound processor by way of a wireless audio transmission link (not explicitly shown in FIG. 2).

Headpiece 206 may be separate from sound processor 204 (i.e., disposed in a separate housing from the housing of sound processor 204), but may be communicatively coupled to sound processor 204 by way of a cable including one or more conductors. For instance, in conventional cochlear implant systems in which headpiece 206 is implemented as a passive headpiece, the cable may be a coaxial cable configured to carry AC power and data signals generated at sound processor 204 to be radiated from an antenna coil disposed within headpiece 206. Conversely, in cochlear implant system implementations in which headpiece 206 is implemented as an active headpiece implementing transcutaneous transmission system 100 described above, the cable may include several conductors (e.g., including one or more twisted pairs for carrying a differential signal) for carrying various power and data signals described herein.

Regardless of whether headpiece 206 is implemented as a passive or an active headpiece, headpiece 206 may include an external antenna (e.g., a coil and/or one or more wireless communication components) configured to facilitate selective wireless coupling of sound processor 204 to cochlear implant 208. Headpiece 206 may additionally or alternatively be used to selectively and wirelessly couple any other external device to cochlear implant 208. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise associated with cochlear implant 208. In this manner, stimulation parameters and/or power signals may be wirelessly transmitted between sound processor 204 and cochlear implant 208 via communication link 214.

Cochlear implant 208 may include any type of implantable stimulator that may be used in association with the systems and methods described herein. For example, cochlear implant 208 may be implemented by an implantable cochlear stimulator. In some alternative implementations, cochlear implant 208 may include a brainstem implant and/or any other type of active implant or auditory prosthesis that may be implanted within a recipient and configured to apply stimulation to one or more stimulation sites located along an auditory pathway of a recipient.

In some examples, cochlear implant 208 may be configured to generate electrical stimulation representative of an audio signal processed by sound processor 204 (e.g., an audio signal detected by microphone 202) in accordance with one or more stimulation parameters transmitted thereto by sound processor 204 by way of headpiece 206. Cochlear implant 208 may be further configured to apply the electrical stimulation to one or more stimulation sites within the recipient via one or more electrodes 212 disposed along lead 210 (e.g., by way of one or more stimulation channels formed by electrodes 212). In some examples, cochlear implant 208 may include a plurality of independent current sources each associated with a channel defined by one or more of electrodes 212. In this manner, different stimulation current levels may be applied to multiple stimulation sites simultaneously (also referred to as "concurrently") by way of multiple electrodes 212.

Figure 3:
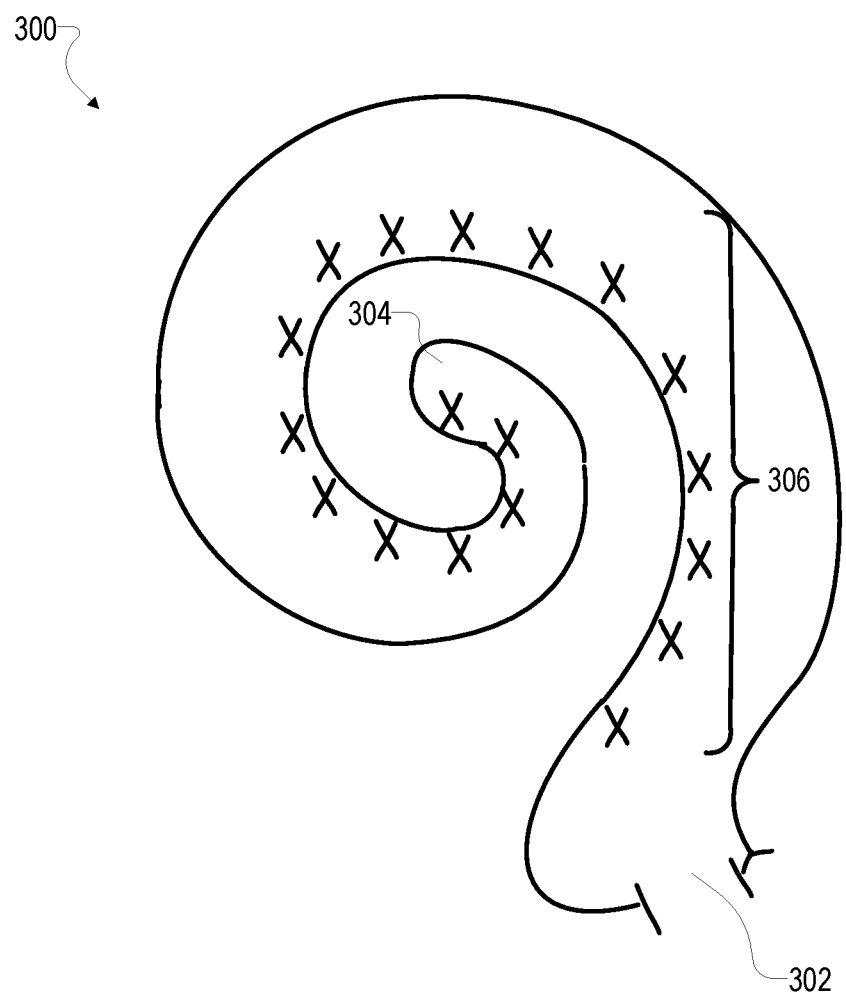
FIG. 3 shows an illustrative schematic structure of the human cochlea according to principles described herein.

FIG. 3 shows an illustrative schematic structure of a human cochlea 300 into which lead 210 may be inserted. As shown in FIG. 3, cochlea 300 is in the shape of a spiral beginning at a base 302 and ending at an apex 304. Within cochlea 300 resides auditory nerve tissue 306, which is denoted by Xs in FIG. 3. Auditory nerve tissue 306 is organized within cochlea 300 in a tonotopic manner. That is, relatively low frequencies are encoded at or near apex 304 of cochlea 300 (referred to as an "apical region") while relatively high frequencies are encoded at or near base 302 (referred to as a "basal region"), Hence, each location along the length of cochlea 300 corresponds to a different perceived frequency, Cochlear implant system 300 may therefore be configured to apply electrical stimulation to different locations within cochlea 300 (e.g., different locations along auditory nerve tissue 306) to provide a sensation of hearing to the recipient. For example, when lead 210 is properly inserted into cochlea 300, each of electrodes 212 may be located at a different cochlear depth within cochlea 300 (e.g., at a different part of auditory nerve tissue 306) such that stimulation current applied to one electrode 212 may cause the recipient to perceive a different frequency than the same stimulation current applied to a different electrode 212 (e.g., an electrode 212 located at a different part of auditory nerve tissue 306 within cochlea 300).

Figure 4:
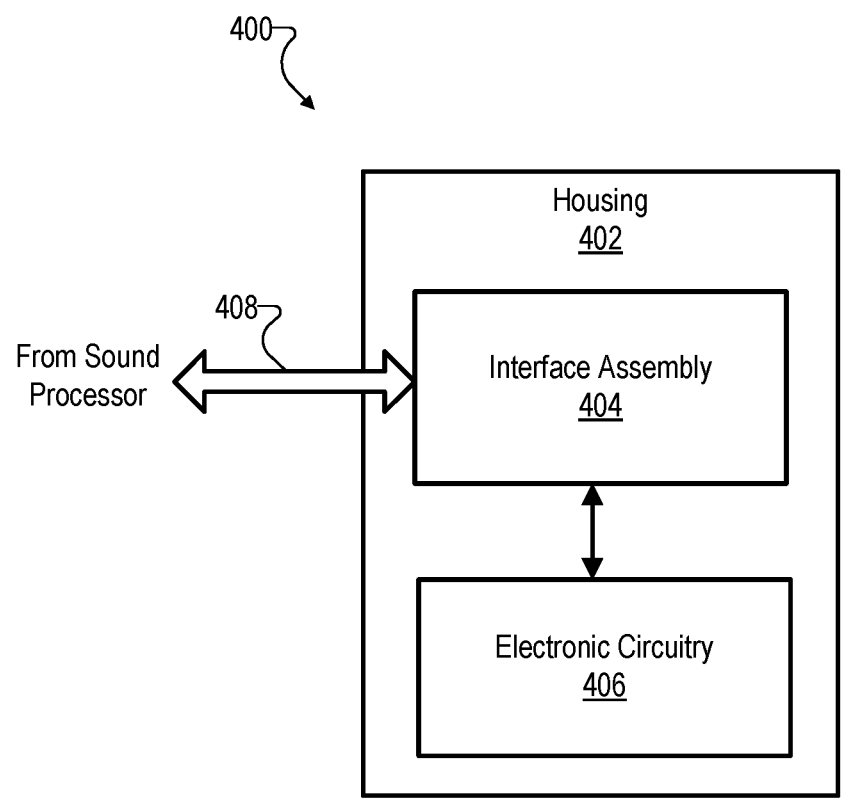
FIG. 4 shows an illustrative active headpiece implementing the transcutaneous transmission system of FIG. 1 and configured to wirelessly transmit power and data to an implantable stimulator according to principles described herein.

FIG. 4 shows an illustrative active headpiece 400 that is an implementation of system 100 and is configured to wirelessly transmit power and data to an implantable stimulator in accordance with principles described herein. Active headpiece 400 may be included within a cochlear implant system such as cochlear implant system 200 and may be configured to wirelessly transmit power (e.g., AC power 104) and data (e.g., forward telemetry data 106) to a cochlear implant (e.g., cochlear implant 208). As shown, active headpiece 400 may include, without limitation, a housing 402, an interface assembly 404, and electronic circuitry 406. Interface assembly 404 and electronic circuitry 406 may be communicatively coupled to one another and may be disposed within (e.g., housed in, integrated into, etc.) housing 402. For example, interface assembly 404 and electronic circuitry 406 may be "disposed within" housing 402, as that term is used herein, if the components comprising interface assembly 404 and electronic circuitry 406 are at least partially contained inside housing 402. In some examples, housing 402 may completely enclose all of the components of interface assembly 404 and/or electronic circuitry 406, whereas, in other examples, at least one component of interface assembly 404 or electronic circuitry 406 may be only partially housed within housing 402 (e.g., such as a connector that protrudes through a wall of housing 402).

Interface assembly 404 may include any connectors, conductors, pads, passive electrical components, active electrical components, mechanical components, and/or other suitable components configured to facilitate active headpiece 400 in exchanging electrical power and/or data with an external device such as a sound processor (not explicitly shown in FIG. 4) that is communicatively coupled with interface assembly 404 by way of a cable 408. The sound processor may be further included within the cochlear implant system in which active headpiece 400 is included, but may be external to housing 402. For example, the sound processor may be a completely separate system component from active headpiece 400 within the cochlear implant system, and may be disposed within a dedicated housing of its own that is separate from housing 402. Other types of external devices employed as part of other types of implantable stimulation systems (besides cochlear implant systems) may similarly be housed separately from implementations of system 100 just as the sound processor is housed separately from active headpiece 400 in this example.

Interface assembly 404 may be configured to exchange any power and/or data signals with the sound processor over cable 408 as may serve a particular implementation. For example, interface assembly 404 may receive DC power from the sound processor over cable 408. Additionally, interface assembly 404 may receive, over cable 408, a self-clocking differential signal comprising a data signal encoded with a clock signal at a clock frequency. The data signal may be representative of data configured for use by a cochlear implant (e.g., cochlear implant 208).

Electronic circuitry 406 may receive the DC power, the self-clocking differential signal, and/or other power or data signals provided by the sound processor by way of interface assembly 404. Upon receiving the power and data signals, electronic circuitry 406 may be configured to recover the data signal and the clock signal from the self-clocking differential signal and to generate, based on the recovered clock signal, one or more synthesized clock signals at one or more carrier frequencies. The one or more carrier frequencies at which the one or more synthesized clock signals are generated may be any suitable frequencies generated in any suitable way, as will be described below. For example, at least one of the one or more carrier frequencies may be distinct from the clock frequency of the recovered clock signal. Having recovered the data signal and the clock signal, electronic circuitry 406 may use the one or more synthesized clock signals to wirelessly transmit AC power based on the DC power and forward telemetry data based on the recovered data signal to the cochlear implant. For example, the AC power and the forward telemetry data may be transmitted by way of different AC signals having the same or different carrier frequencies, or may be transmitted by way of a single AC signal having a particular carrier frequency.

In some examples, along with receiving data signals from the sound processor, electronic circuitry 406 may also provide data signals to the sound processor. For example, as will be described in more detail below, a back telemetry data signal may be received from the cochlear implant over a wireless link between active headpiece 400 and the cochlear implant. The back telemetry data signal may be received by active headpiece 400 and sent to the sound processor over cable 408.

Figure 5:
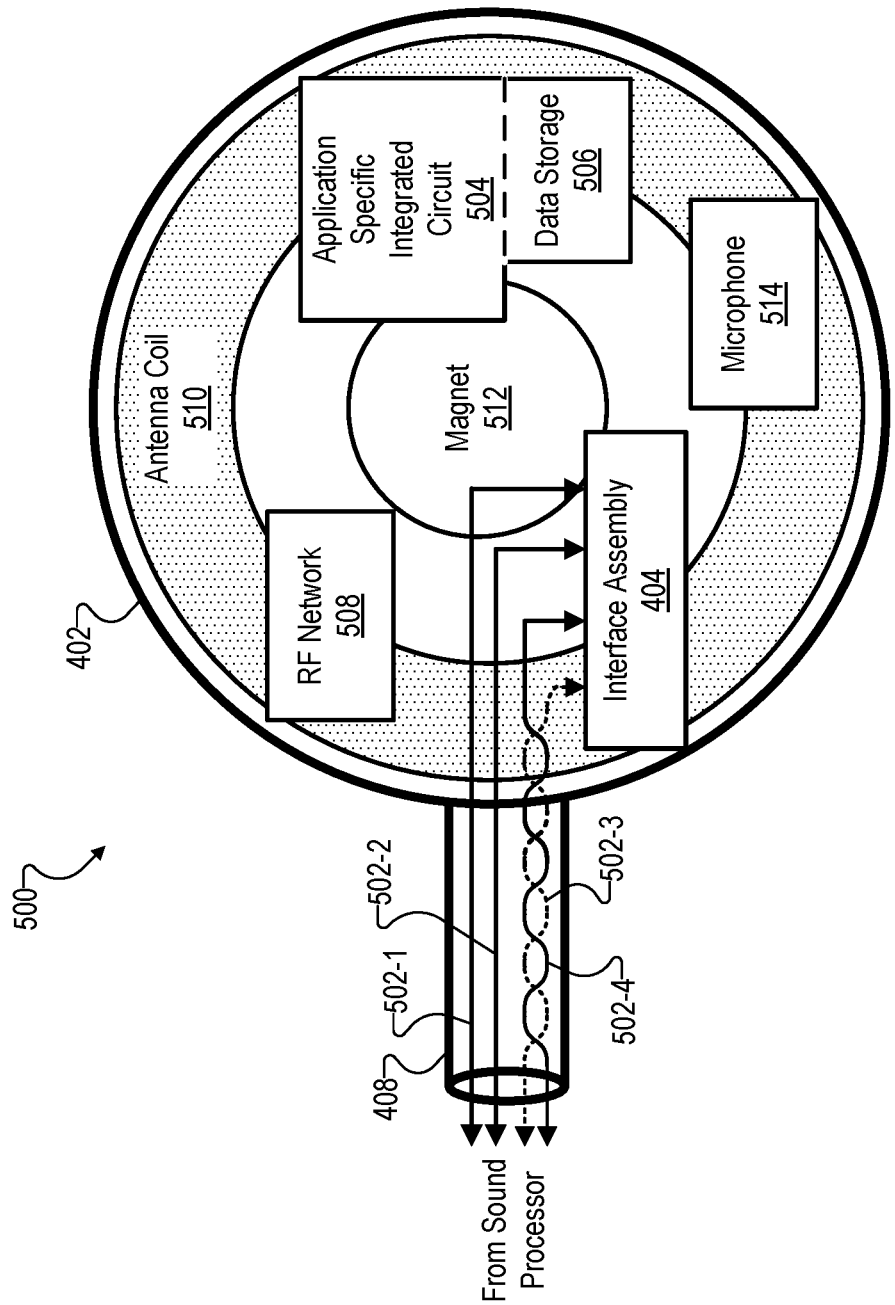
FIG. 5 shows an illustrative implementation of the active headpiece of FIG. 4 according to principles described herein.

FIG. 5 shows an illustrative implementation 500 of active headpiece 400. It will be understood that implementation 500 illustrates just one particular way that an active headpiece for wirelessly transmitting power and data to a cochlear implant may be implemented. As such, implementation 500 may be modified in various ways (e.g., ways described herein or any other suitable way) to create other suitable implementations of active headpiece 400. For example, additional or fewer components as shown in implementation 500 may be used in various other implementations of active headpiece 400. Implementation 500 of active headpiece 400 will also be referred to herein as active headpiece 500.

As shown within cable 408, a plurality of conductors 502 (e.g., conductors 502-1 through 502-4) may be included within active headpiece 500 for exchanging power and/or data signals between a sound processor (not explicitly shown in FIG. 5) and interface assembly 404. Interface assembly 404 is shown to be disposed within housing 402 (e.g., implemented as a circular housing within active headpiece 500) along with various electronic circuitry and other components also disposed within the housing. For example, as shown, housing 402 further encloses an application specific integrated circuit ("ASIC") 504 associated with a data storage facility 506, a radio frequency ("RF") network 508, an antenna coil 510, a magnet 512, and a microphone 514. While explicit connections among these other components are not explicitly illustrated, it will be understood that the electronic elements housed within housing 402 may be selectively and communicatively coupled with one another in any manner as may serve a particular implementation so as to be able to perform operations described herein.

Conductors 502 may be implemented as wires or other suitable conductors enclosed within an insulative casing of cable 408. In some examples, a 4-wire interface between the sound processor and active headpiece 500 may be employed that includes the four conductors 502 illustrated in FIG. 5. In other examples, additional conductors beyond conductors 502 of the 4-wire interface may also be used. Conductor 502-1 may be used to carry DC power from the sound processor to active headpiece 500 and/or to carry an electrical signal (e.g., a back telemetry data signal, a microphone signal, etc.) from active headpiece 500 back to the sound processor. Conductor 502-2 may be used in conjunction with conductor 502-1 to serve as a ground reference. Conductors 502-3 and 502-4 may be implemented by a twisted pair of wires so as to facilitate an efficient and low-emission wired transmission of differential signals such as a self-clocking differential signal sent from the sound processor to active headpiece 500. To illustrate, conductors 502-3 and 504-4 are depicted as being twisted around one another throughout cable 408. In other examples, conductors 502 may be implemented in other ways such as using coaxial conductors or the like.

ASIC 504 may include various logic, power supplies, clock generation and/or derivation circuitry (e.g. clock control loops, etc.), and/or other electronic circuitry used to perform the operations described herein. ASIC 504 will be described below in more detail. However, it will be understood that the functionality provided by ASIC 504 (as well as data storage facility 506) may be provided to active headpiece 500 in any suitable manner. For example, rather than being performed within a special-purpose ASIC as will be described below, the functionality of ASIC 504 and/or data storage facility 506 may be performed by discrete components or integrated circuits, by discrete logic circuitry, by a general purpose microprocessor or other computing component, by programmable hardware such as a field programmable gate array (FPGA"), by a combination thereof, or by any other passive or active electronic circuitry as may serve a particular implementation.

Data storage facility 506 may be associated with ASIC 504 in any suitable way and may be used to store any suitable data. For example, data storage facility 506 may be integrated within (i.e., built into) ASIC 504 in certain implementations, and may be implemented as an external storage device (e.g., a discrete storage device included within housing 402 such as a flash memory device, an EEPROM device, or the like) in other implementations. In implementations in which data storage facility 506 is implemented on a chip separate from ASIC 504, ASIC 504 may include a data storage interface (e.g., a dedicated communication interface) for communicatively coupling ASIC 504 with the external storage device upon which data storage facility 506 is implemented.

Data storage facility 506 may be configured to maintain any data received, generated, managed, maintained, used, and/or transmitted by ASIC 504, active headpiece 500, or the cochlear implant system within which active headpiece 500 is included. For example, data storage facility 506 may hold configuration values for ASIC 504 and the circuitry implemented therein. For instance, register values configuring clock frequencies to be generated and used by active headpiece 500 may be stored in data storage facility 506 and loaded into registers within ASIC 504 upon system startup (e.g., when active headpiece 500 operates in a setup mode as will be described in more detail below). As another example, data storage facility 506 may store data used by the sound processor, such as data (e.g., backup data) representative of sound processing parameters associated with a particular recipient, sound processing programs used by the sound processor, or the like.

RF network 508 may include a network of passive components (e.g., capacitors, inductors, transformers, etc.) configured to facilitate antenna coil 510 in transcutaneously exchanging wireless signals with a corresponding antenna coil associated with a cochlear implant implanted within the recipient. For example, RF network 508 may include passive electronic circuitry that achieves an effective and efficient impedance for antenna coil 510 in a manner similar to or the same as that employed by conventional passive headpieces.

Antenna coil 510 may be disposed along an outer perimeter of active headpiece 500, as shown. In some examples, antenna coil 510 may represent a single antenna coil comprised within active headpiece 500. In such examples, the electronic circuitry within active headpiece 500 (e.g., ASIC 504, RF network 508, etc.) may wirelessly transmit both the AC power and the forward telemetry data by way of the single antenna coil represented by antenna coil 510. In other examples, antenna coil 510 may represent both a first antenna coil and a second antenna coil distinct from the first antenna coil, both of which are comprised within active headpiece 500. In these examples, the electronic circuitry within active headpiece 500 may wirelessly transmit the AC power at a first carrier frequency by way of the first antenna coil, and may wirelessly transmit the forward telemetry data (e.g., by way of a data-modulated AC signal at the second carrier frequency) by way of the second antenna coil. Additionally, one or more additional antenna cons such as an antenna coil dedicated to receiving a back-telemetry wireless signal from the cochlear implant may also be included in the plurality of antenna coils represented by antenna coil 510.

Magnet 512 may be included within active headpiece 500 in the same way and for the same reason as magnets may be included in conventional passive headpieces. Specifically, magnet 512 may be used to align active headpiece 500 with a cochlear implant implanted under the skin of the recipient, as well as to hold active headpiece 500 in place on the recipient's head. In other examples, other suitable alignment and/or attachment mechanisms or techniques may be employed in addition to or as an alternative to magnet 512.

In certain examples, active headpiece 500 may include microphone 514 to replace or augment the detection of sound performed by one or more microphones disposed in other locations. In examples in which active headpiece 500 includes microphone 514 disposed within housing 402, microphone 514 may be communicatively coupled to the sound processor by way of cable 408. For example, microphone 514 may be configured to detect sound presented to the recipient and to generate and provide, to the sound processor by way of one or more of conductors 502 (e.g., an additional conductor 502 not explicitly shown), a signal representative of the sound. In such examples, the data signal representative of data configured for use by the cochlear implant (i.e., the data signal comprised within the self-clocking differential signal received from the sound processor) may be generated by the sound processor based on the signal representative of the sound generated and provided by microphone 514.

While various components that may be included within active headpiece 400 have been illustrated and described in reference to implementation 500 in FIG. 5, it will also be noted that certain components may be advantageously omitted from other implementations of active headpiece 400. For example, because electronic circuitry included within active headpiece 400 (e.g., within ASIC 504) may be configured to recover a clock signal received from the sound processor and to generate synthesized clock signals based on the recovered clock signal, no crystal oscillator or other such clock generation components for generating clock signals from scratch may be employed within certain implementations of active headpiece 400. To the contrary, all clock signals generated within and/or used by electronic circuitry in these implementations of active headpiece 400 may be derived from a dock signal generated by an oscillator included within the sound processor. In like manner, active headpiece 400 may be configured to be powered exclusively by power received from the sound processor, such that no battery may be disposed within housing 402 of active headpiece 400 in certain implementations. As mentioned above, while omitting these components may provide various advantages (e.g., reduced design constraints, improved power efficiency, reduced emissions, etc.) under certain circumstances, there may be other circumstances where it is desirable to integrate components such as independent clock generation circuitry and/or battery power sources into implementations of active headpiece 400 or other implementations of system 100. In these examples, such components may therefore be included.

Electronic circuitry within active headpiece 500 may perform any of various operations described herein. As mentioned above, many such operations may be performed by application specific circuitry built into a special purpose chip such as ASIC 504, or by other suitable electronic circuitry. Specifically, for example, ASIC 504 may be configured in certain implementations to receive (e.g., by way of interface assembly 404 from a sound processor external to housing 402) DC power and/or a self-clocking differential signal comprising a data signal encoded with a clock signal at a clock frequency. The data signal may be representative of data configured for use by a cochlear implant included within the cochlear implant system and configured to be implanted within the recipient. ASIC 504 may be further configured to recover, from the self-clocking differential signal, the data signal and the clock signal at the clock frequency. Based on the recovered dock signal at the clock frequency, ASIC 504 may be configured to generate one or more synthesized clock signals at one or more carrier frequencies, at least one of which may be distinct from the recovered clock frequency. ASIC 504 may be configured to wirelessly transmit, to the cochlear implant using the one or more synthesized clock signals at the one or more carrier frequencies, AC power based on the DC power and forward telemetry data based on the recovered data signal.

As has been mentioned, the configuration by way of which the AC power (e.g., an implementation of AC power 104) and the forward telemetry data (e.g., an implementation of forward telemetry data 106) may be wirelessly transmitted to an implantable stimulator such as a cochlear implant may take various forms as may serve a particular implementation. As one example, the electronic circuitry of a transcutaneous transmission system (e.g., an active headpiece of a cochlear implant system) may be configured to generate, based on a recovered clock signal at the clock frequency, a plurality of synthesized clock signals at a plurality of carrier frequencies. As such, the wireless transmitting of the AC power and the forward telemetry data may be performed using the plurality of synthesized clock signals by wirelessly transmitting a first AC signal that carries the AC power at a first carrier frequency of a first synthesized clock signal, and wirelessly transmitting, at a second carrier frequency of a second synthesized clock signal, a second AC signal onto which the forward telemetry data is modulated. This type of example will be illustrated below with respect to FIGS. 6-7. As another example, the wireless transmitting of the AC power and the forward telemetry data may be performed using a single synthesized clock signal by wirelessly transmitting a data-modulated AC signal that modulates the forward telemetry data onto the AC power carried at the carrier frequency of the synthesized clock signal. This type of example will be illustrated below with respect to FIGS. 9-10. As will be further described below, FIG. 8 illustrates certain modes of operation for the transcutaneous transmission system that may be implemented in the examples of FIGS. 6-7 or the examples of FIGS. 9-10.

Figure 6:
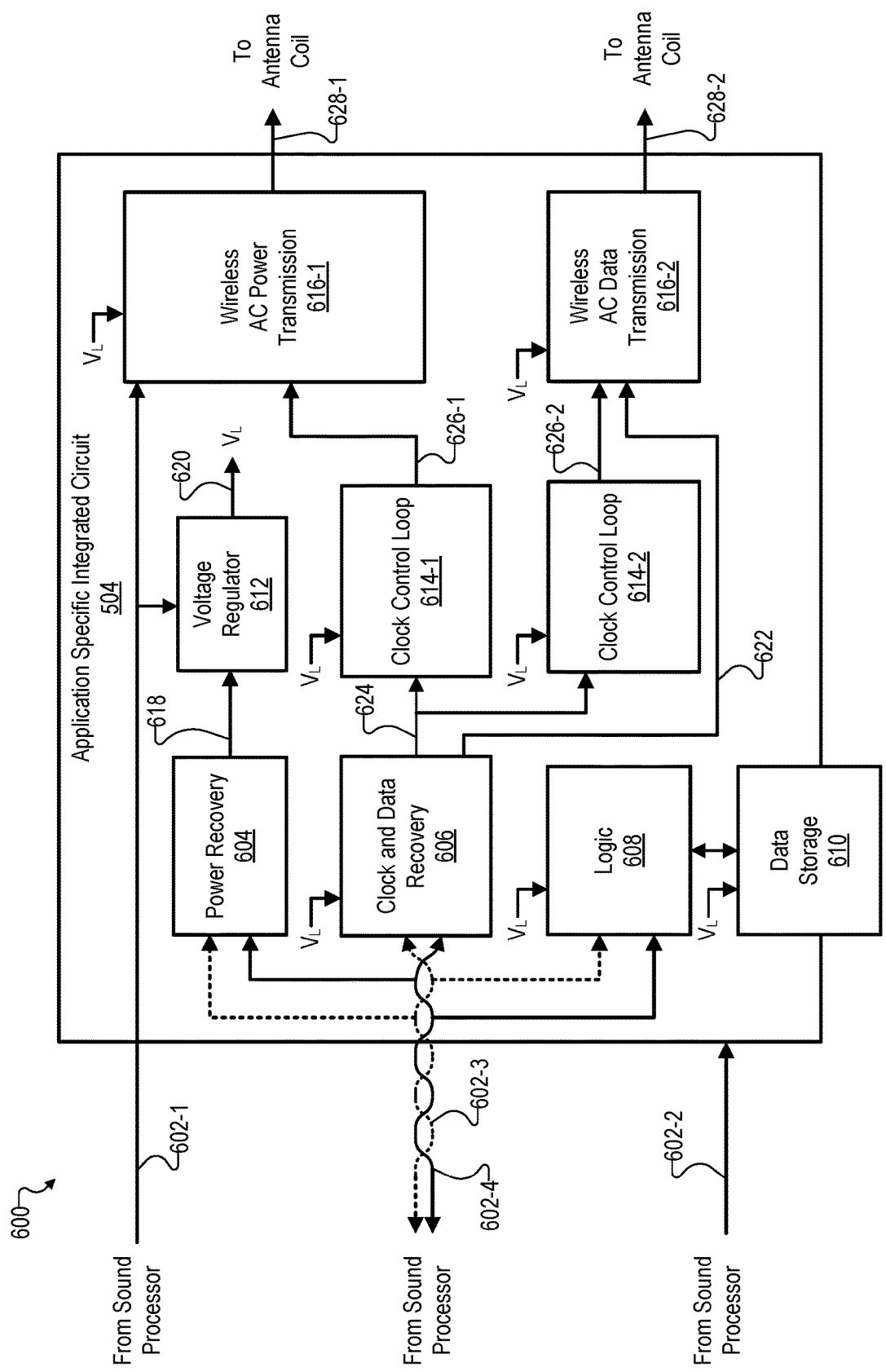
FIG. 6 shows one illustrative implementation of an application specific integrated circuit for use within the active headpiece of FIG. 4 according to principles described herein.

FIG. 6 shows one illustrative implementation 600 of an ASIC 504 for use within an implementation of active headpiece 400 (e.g., implementation 500, etc.). As shown, implementation 600 of ASIC 504 may include various inputs, outputs, components, functional blocks, intermediary signals, and so forth, that enable ASIC 504 to perform various operations described herein. For example, as shown, ASIC 504 may receive various inputs 602 (e.g., inputs 602-1 through 602-4) for use by a variety of functional blocks including, without limitation, a power recovery facility 604, a clock and data recovery facility 606, a logic facility 608, a data storage facility 610, a voltage regulator 612, two clock control loops 614 (e.g., clock control loops 614-1 and 614-2), two wireless AC power transmission facilities 616 (i.e., a wireless AC power transmission facility 616-1 and a wireless AC data transmission facility 616-2), and any other facilities, components, etc. as may serve a particular implementation.

Functional blocks 604 through 616 may be implemented in any suitable way, such as by dedicated logic and other hardware built into ASIC 504 (e.g., very-large-scale integration ("VLSI") hardware, mixed signal integrated circuit hardware, system on a chip ("SoC") hardware, mixed signal SoC hardware, etc.). Additionally, each functional block 604 through 616 may be selectively and communicatively coupled to one another in any suitable way, including by way of the connections shown in FIG. 6 or by way of other suitable connections.

Inputs 602 may be received by ASIC 504 from a sound processor by way of interface assembly 404, described above. Specifically, input 602-1 may correspond to (e.g., may be the same as or derived based on) a signal carried by conductor 502-1, input 602-2 may correspond to a signal carried by conductor 502-2, input 602-3 may correspond to a signal carried by conductor 502-3, and input 602-4 may correspond to a signal carried by conductor 502-4. Just as conductors 502-3 and 502-4 may be configured to facilitate proper transmission of a differential signal in the ways described above (e.g., by forming a twisted pair of conductors, etc.), PCB traces around ASIC 504 and/or conduction paths internal to ASIC 504 may be specially configured to carry inputs 602-3 and 602-4 as a differential signal by, for example, being matched in length, impedance, and the like.

Power recovery facility 604 may receive a differential signal (e.g., a self-clocking differential signal) from inputs 602-3 and 602-4 and, based on DC power included within the differential signal, may generate a recovered power 618, which may be a fixed DC power having a voltage that is fixed at a particular level (e.g., 1.0 V). In other words, recovered power 618 may be derived from a self-clocking differential signal received by active headpiece 400 from the sound processor, rather than, for example, from the DC power sent by the sound processor and received by ASIC 504 as input 602-1, or from any internal battery or other power source within active headpiece 400.

During normal operation, when the cochlear implant system is providing stimulation to the recipient to invoke the sensation of hearing, recovered power 618 may be used by voltage regulator 612 to derive a logic power 620 (abbreviated in FIG. 6 as "$V_L$" for "$V_{Logic}$"). As shown, logic power 620 may be used throughout ASIC 504 to power some or all of the other facilities and functional blocks within ASIC 504. As such, in these examples, ASIC 504 may use the fixed DC power of recovered power 618 to perform the recovery of the data signal and the dock signal and to perform the generation of the different synthesized dock signals described below.

Voltage regulator 612 may be implemented by any suitable type of voltage regulator (e.g., a linear regulator such as a linear drop-out ("LDO") regulator, a switching regulator, a hybrid regulator, etc.) configured to generate logic power 620 as a dean and stable power rail. As described above, voltage regulator 612 may generate logic power 620 based on recovered power 618 in certain examples (e.g., during normal operation). In other examples, however, voltage regulator 612 may generate logic power 620 based on the DC power sent by the sound processor and received as input 602-1. Thus, as shown, input 602-1 may also be connected as an input to voltage regulator 612 along with recovered power 618 so that voltage regulator 612 may opt to use either or both power sources in different implementations or when operating in different modes.

During normal operation, the DC power coming in on input 602-1 may be variable DC power having a variable voltage level that changes, for example, based on a sound level being picked up by a microphone in the cochlear implant system. For instance, the DC power coming in on input 602-1 may be 0.5 V when the recipient is in a relatively quiet location, or 3.0 V when the recipient is in a relatively noisy location. This wide variability in the DC power of input 602-1 during normal operation may make it difficult or impractical for logic power 620 to be derived from the variable DC power, particularly if the desired voltage level for logic power 620 is within the range across which the variable DC power varies (e.g., as 1.0 V is within the range of 0.5 V to 3.0 V). For this reason, it may be convenient, although not required, for voltage regulator 612 to use recovered power 618 to generate logic power 620 during normal operation of the cochlear implant system. However, when the cochlear implant system is in modes of operation other than the normal mode of operation (e.g., a setup mode of operation), the DC power coming in on input 602-1 from the sound processor may have a narrower range, or may be a fixed DC power having a voltage that is fixed at a particular level. As such, particularly in these other modes of operation, voltage regulator 612 may use the fixed DC power on input 602-1 to generate logic power 620 for performing the recovery of the data signal and the clock signal and performing the generation of the synthesized clock signals. In still other examples, a battery included within active headpiece 400 may be used to generate power from which voltage regulator 612 may derive logic power 620.

Just as power recovery facility 604 recovers power from a self-clocking differential signal coming in on inputs 602-3 and 602-4, clock and data recovery facility 606 may also be configured to perform a recovery operation from the self-clocking differential signal sent by the sound processor on these inputs. However, rather than recovering power, clock and data recovery facility 606 may recover a data signal 622 and a clock signal 624 that is encoded with data signal 622 using a particular encoding technique used by the sound processor. For example, data signal 622 may have been encoded with clock signal 624 using a clock encoding technique (e.g., a zero DC balance encoding technique), and clock and data recovery facility 606 may be configured to recover data signal 622 and clock signal 624 in accordance with the clock encoding technique. Different zero DC balance or other clock encoding techniques may be employed in different implementations. For instance, data signal 622 may be encoded with clock signal 624 using a Manchester, biphase-mark, or other clock encoding technique, and clock and data recovery facility 606 may be configured to recover data signal 622 and clock signal 624 in accordance with the Manchester, biphase-mark, or other clock encoding technique. In other examples, various other established or proprietary clock encoding schemes (e.g., differential Manchester encoding, other types of biphase encoding, other zero DC balance encoding techniques, etc.) may be employed as may serve a particular implementation. Clock and data recovery facility 606 may operate using a clock control loop such as a phase-locked loop ("PLL"), a delay-locked loop ("DLL"), or any other suitable clock recovery circuit used to decode self-clocking differential signals based on the encoding scheme with which they are encoded.

Clock control loops 614 may also be implemented using PLLs, DLLs, and/or other suitable clock control loops configured to synthesize clock signals at programmable clock frequencies (e.g., arbitrary clock frequencies, clock frequencies within a particular range, etc.) that may be different from a clock frequency of an input signal used to synthesize the clock signals. For example, if clock signal 624 has a clock frequency of 1.0 MHz, clock control loop 614-1 may synthesize a clock signal 626-1 at a clock frequency of 5.0 MHz while clock control loop 614-2 may synthesize a clock signal 626-2 at a clock frequency of 49.0 MHz. It will be understood that these frequencies are given as examples only. As will be described in below, it may be advantageous in other examples to transmit power and/or forward telemetry data at other frequencies, including frequencies significantly lower than 49.0 MHz. In other examples, at least one of synthesized clock signals 626 may have the same clock frequency as recovered clock signal 624 and/or may have a lower clock frequency than that of recovered clock signal 624.

Clock control loops 614 may be programmable by writing registers or otherwise setting values associated with the clock control loop circuitry to define the expected clock frequency of the input clock signal (i.e., clock signal 624) and the desired clock frequency of the output clock signal (i.e., clock signals 626-1 or 626-2). Values for such registers may be stored within data storage 610. As such, the values may be set to the registers, as well as read from and/or written (e.g., overwritten, reprogrammed, etc.) to data storage 610, when active headpiece 400 is in a setup mode of operation (e.g., at startup and/or before shutting down).

In this way, active headpiece 400 may provide a large amount of flexibility for compatibility with a wide variety of different sound processors and/or cochlear implants configured to operate at different clock frequencies. For example, a particular sound processor configured to generate a self-clocking differential signal at a first particular clock frequency may be made to be compatible with various cochlear implants configured to receive power and/or data transmissions on various different carrier frequencies by properly configuring clock control loops 614 in software (e.g., by properly writing the appropriate registers) without any change in hardware (e.g., such as replacing one crystal oscillator with another). As another example, a particular cochlear implant configured to receive power and/or data transmissions at a particular carrier frequency (or plurality of carrier frequencies) may be made to be compatible with various sound processors configured to generate self-clocking differential signals at different clock frequencies by similarly configuring dock control loops 614.

As shown, dock signal 626-1 may be used by wireless AC power transmission facility 616-1 as a carrier frequency for a power transmission output 628-1, while dock signal 626-2 may be used by wireless AC data transmission facility 616-2 as a carrier frequency for a data transmission output 628-2. For example, outputs 628 (i.e., power transmission output 628-1 and data transmission output 628-2) may be implemented as RF signals that may carry a significant amount of power (e.g., power sufficient to power the cochlear implant) and/or may include modulated forward telemetry data. As such, clock signals 626 may each be implemented with any clock frequency as may serve as a suitable power carrier frequency (for wireless AC power transmission facility 616-1) or a suitable data carrier frequency (for wireless AC data transmission facility 616-2) in a particular implementation. For instance, in some examples, the clock frequency of clock signals 626 may be programmed to a frequency upon which emission regulations (e.g., FCC regulations in the United States) allow cochlear implant systems to transmit.

It may be advantageous, in certain examples, for the clock frequency of clock signal 626-2 (i.e., the carrier frequency at which data output 628-2 is to be transmitted) to be programmed to be significantly higher (e.g., at least twice as high) as the clock frequency of clock signal 626-1 (i.e., the carrier frequency at which power output 628-1 is to be transmitted). For example, data at a particular clock rate (e.g., the clock rate of dock signal 624) may best be modulated onto a carrier signal when the carrier frequency of the carrier signal is significantly faster than the rate at which the data is clocked. As such, it may be desirable for the carrier frequency of data output 628-2 to be relatively high. Because this transmission may use a relatively low voltage and low power, it may be relatively efficient to employ the high carrier frequency. In contrast, for power output 628-1, it may be much more important, for the sake of efficiency, for the carrier frequency to be relatively low. For example, switching power consumed by wireless AC power transmission facility 616-1 may be significantly reduced by driving power output 628-1 at a relatively low carrier frequency. Additionally, power output 628-1 may be tuned with a large quality factor ("Q factor") so as to oscillate efficiently because of the fact that power and data are sent by active headpiece 400 separately at different frequencies, rather than by modulating the data onto the power signal.

As shown, wireless AC power transmission 616-1 may generate power output 628-1 based on the DC power coming into ASIC 504 on input 602-1. As mentioned above, this DC power may be a variable DC power that changes based on the sound level experienced by the recipient in whatever environment the recipient is in (at least when operating in the normal operation mode). Accordingly, it will be understood that power output 628-1 may provide a variable amount of power to the cochlear implant while data output 628-2 may be generated at a fixed voltage.

Logic facility 608 may represent any logic circuitry included within ASIC 504 that has not already been described as part of one of the other facilities. Logic facility 608 may perform various functions including, for example, interfacing with data storage facility 610. Data storage facility 610 may implement data storage facility 506 (described above) and, as such, may be an integrated data storage facility built into ASIC 504 in some examples, and an external data storage facility with which ASIC 504 (e.g., logic facility 608) is configured to interface and communicate in other examples. For instance, logic facility 608 may be configured to provide read/write access to the sound processor when active headpiece 400 is in a setup mode of operation, and to make data storage facility 610 transparent to the sound processor when active headpiece 400 is in a normal mode of operation.

Figure 7:
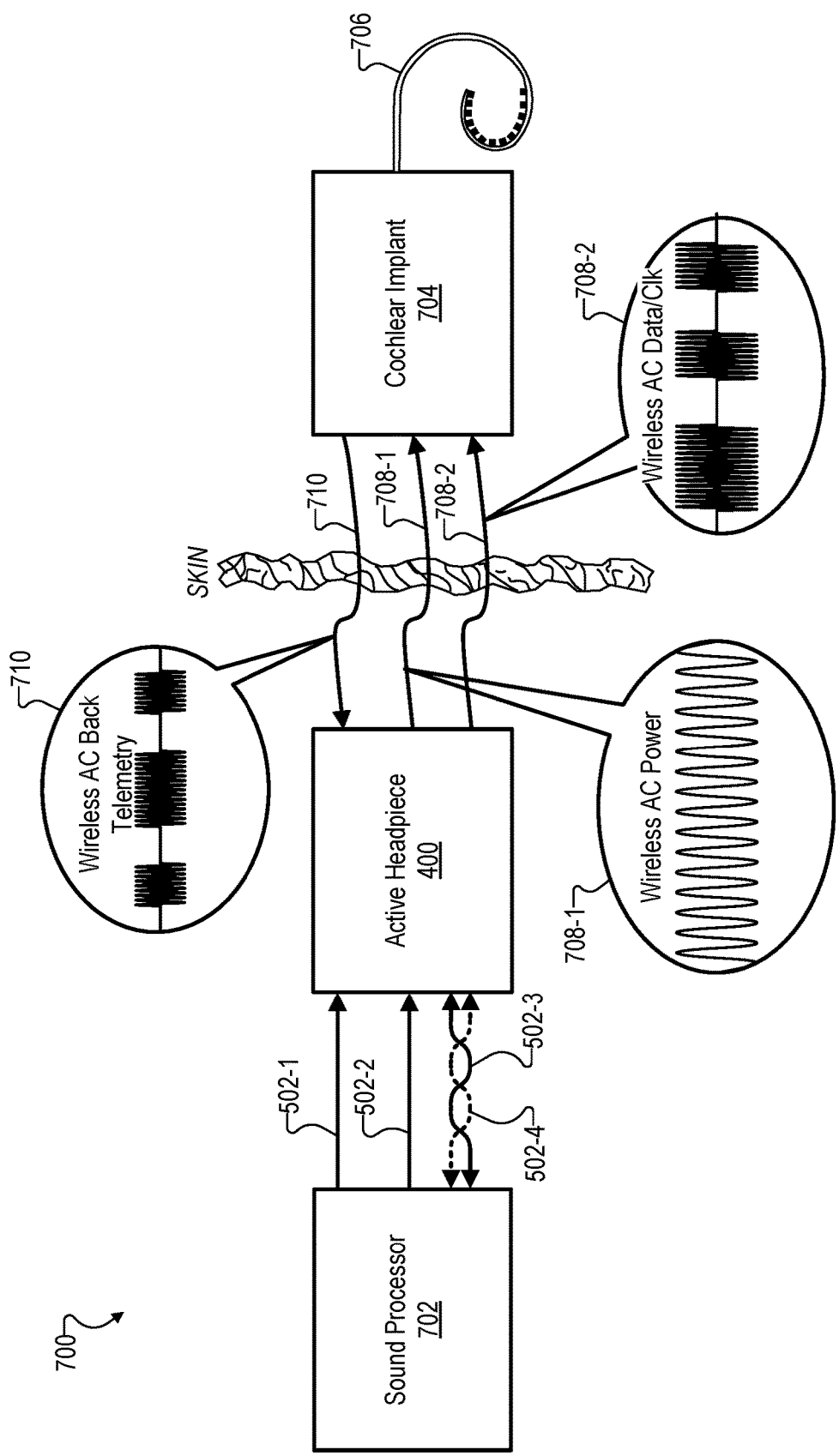
FIG. 7 shows one illustrative configuration in which the active headpiece of FIG. 4 interoperates with a sound processor and a cochlear implant within an illustrative cochlear implant system according to principles described herein.
Figure 8:
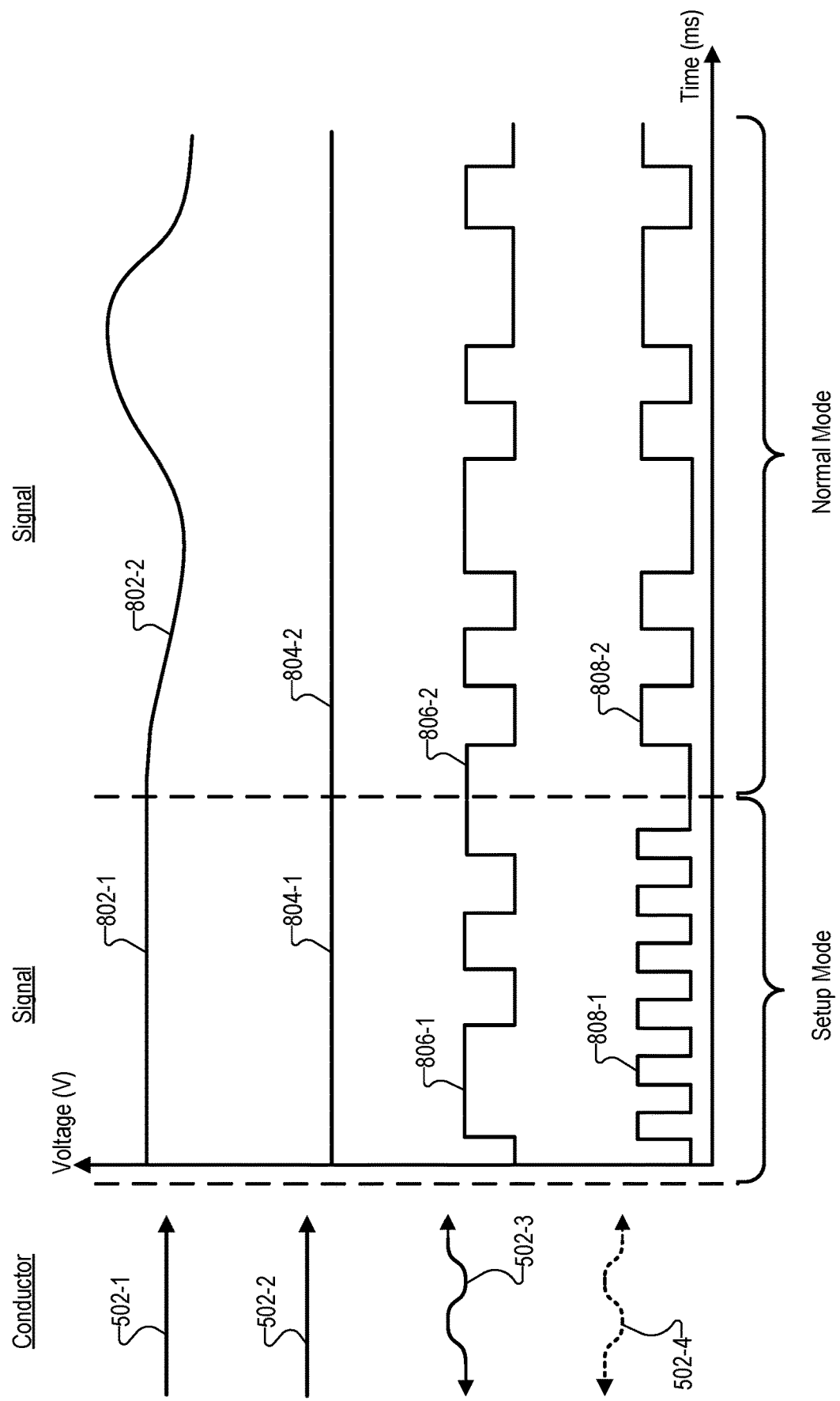
FIG. 8 shows illustrative waveforms that may be transmitted when an active headpiece is operating in different modes of operation according to principles described herein.

FIG. 7 shows one illustrative configuration 700 in which active headpiece 400 interoperates with a sound processor 702 and a cochlear implant 704 within an exemplary cochlear implant system. The cochlear implant system comprising the components of configuration 700 may be similar to cochlear implant system 200, described above. For example, sound processor 702 may be analogous to sound processor 204, cochlear implant 704 may be analogous to cochlear implant 208, and a lead 706 coupled with cochlear implant 704 may be analogous to lead 210. In configuration 700, active headpiece 400 may perform the role described above in relation to headpiece 206, However, unlike headpiece 206, which may be implemented as a passive headpiece, active headpiece 400 is implemented as an active headpiece (and an implementation of transcutaneous transmission system 100) that is configured to perform the active operations described herein.

As shown in FIG. 7, a 4-conductor interface between sound processor 702 and active headpiece 400, which may be implemented in two separate housings, may be employed. Specifically, conductors 502 may serve to electrically and communicatively couple sound processor 702 to active headpiece 400. As mentioned above, conductors 502 may carry any power and/or data signals as may serve a particular implementation. While, in some examples, conductors 502 may each be dedicated to a single purpose (e.g., to carrying a single type of power or data signal), conductors 502 may, in other examples, be configured to carry different types of power or data signals at different times in accordance with a time domain multiplexing scheme. For instance, in some implementations, at least two modes of operation may be defined for the cochlear implant system, and conductors 502 may have distinct purposes in the different modes of operation.

To illustrate, FIG. 8 shows illustrative waveforms that may be transmitted on conductors 502 in configuration 700 when active headpiece 400 is operating in different exemplary modes of operation. Specifically, each conductor 502-1 through 502-4 is shown along a vertical axis next to a respective pair of waveforms depicting an exemplary voltage of the conductor with respect to time during a setup mode of operation (waveforms ending in "-1") and during a normal mode of operation (waveforms ending in "-2").

For example, waveform 802-1 illustrates a voltage with respect to time for conductor 502-1 during the setup mode of operation, while waveform 802-2 illustrates a voltage with respect to time for conductor 502-1 during the normal mode of operation. Similarly, waveform 804-1 illustrates a voltage with respect to time for conductor 502-2 during the setup mode of operation, while waveform 804-2 illustrates a voltage with respect to time for conductor 502-2 during the normal mode of operation. Waveform 806-1 illustrates a voltage with respect to time for conductor 502-3 during the setup mode of operation, while waveform 806-2 illustrates a voltage with respect to time for conductor 502-3 during the normal mode of operation. Waveform 808-1 illustrates a voltage with respect to time for conductor 502-4 during the setup mode of operation, while waveform 808-2 illustrates a voltage with respect to time for conductor 502-4 during the normal mode of operation.

Active headpiece 400 is configured to operate in one mode of operation at a time from a plurality of supported modes of operation including, without limitation, the setup mode of operation and the normal mode of operation illustrated in FIG. 8.

In the setup mode of operation, interface assembly 404 of active headpiece 400 may receive DC power by way of conductors 502-1 and 502-2 (conductor 502-2 serving as a ground reference for the voltage on conductor 502-1), a setup data signal by way of conductor 502-3, and a setup clock signal by way of conductor 502-4. Thus, as shown, waveform 802-1 may represent a fixed DC voltage (e.g., 1.0 V), waveform 804-1 may represent a fixed ground reference (i.e., at 0 V), and waveform 806-1 may represent a setup data signal that is toggling with respect to waveform 808-1, which may represent a setup clock signal. Even though, as described above, conductors 502-3 and 502-4 may be length-matched, combined in a twisted pair, or otherwise configured to carry differential signals, FIG. 8 illustrates that, in the setup mode of operation, the setup data and clock signals carried by these conductors may be implemented as two single-ended signals, rather than as a single differential signal. As such, while operating in the setup mode of operation, active headpiece 400 may perform one or more system setup operations based on the setup data signal and the setup clock signal, rather than, for example, performing the operations of recovering of the data signal and the clock signal from a self-clocking differential signal, generating one or more synthesized clock signals, wirelessly transmitting AC power and/or forward telemetry data, and so forth as described above.

For example, the one or more system setup operations performed in the setup mode of operation may include register configuration operations to setup clock control loop circuits (e.g., clock control loops 614) to properly generate the first and second synthesized clock signals to generate desired carrier frequencies during the normal mode of operation. As another example, the one or more system setup operations may include data reading operations and/or data writing operations to retrieve data from and/or store data to data storage facility 610. For example, if data storage facility 610 is implemented in integrated data storage within ASIC 504, the system setup operations may involve reading from and/or writing to the integrated data storage. Conversely, if data storage facility 610 is implemented in data storage external to ASIC 504, the system setup operations may involve reading from and/or writing to the external data storage.

In the normal mode of operation, interface assembly 404 of active headpiece 400 may receive DC power by way of conductors 502-1 and 502-2 (conductor 502-2 serving as a ground reference for the voltage on conductor 502-1), and a self-clocking differential signal by way of conductors 502-3 and 502-4. Thus, as shown in FIG. 8, waveform 802-2 may represent a variable DC voltage (e.g., ranging from 0.5 V to 3.0 V as the intensity of sound in the environment changes), waveform 804-2 may represent a fixed ground reference (i.e., at 0 V), and waveforms 806-2 and 808-2 may collectively represent the self-clocking differential signal comprising the data signal encoded with the clock signal at the clock frequency. Accordingly, as shown, waveforms 806-2 and 808-2 represent a differential signal in which the voltage on each conductor is always at a voltage level opposite the voltage level on the other conductor. As such, while operating in the normal mode of operation, active headpiece 400 may perform the recovery of the data signal and the clock signal from the self-clocking differential signal, the generation of the one or more synthesized clock signals, the wireless transmission of the AC power and the data-modulated AC signal, and so forth as has been described.

It will be understood that the waveforms in FIG. 8 are not drawn to scale. For example, the varying of the voltage on waveform 802-2 may occur on a much larger time scale than the toggling of the differential signal represented by waveforms 806-2 and 808-2.

Active headpiece 400 may operate within the setup mode or the normal mode at any point in time as may serve a particular implementation. For instance, in some implementations, active headpiece 400 may operate within the setup mode for a few milliseconds right when the cochlear implant system is powering up and/or when the cochlear implant system is powering down, while operating in the normal mode the remainder of the time the cochlear implant system is powered on.

Returning to FIG. 7, along with the 4-conductor interface between sound processor 702 and active headpiece 400 described above, configuration 700 further illustrates a wireless, transcutaneous interface between active headpiece 400 and cochlear implant 704. Specifically, a wireless AC power signal 708-1 and a data-modulated wireless AC signal 708-2 may be transmitted through the skin from active headpiece 400 to cochlear implant 704, while a back telemetry AC signal 710 may be transmitted through the skin from cochlear implant 704 back to active headpiece 400. These signals may be generated and transmitted via one or more coil antennas in any of the ways described herein.

Illustrative waveforms that show the shape of wireless AC power signal 708-1, data-modulated wireless AC signal 708-2, and back telemetry AC signal 710 are broken out from each signal in FIG. 7. In particular, these waveforms illustrate wireless AC power signal 708-1, data-modulated wireless AC signal 708-2, and back telemetry AC signal 710 as implemented when the cochlear implant system is operating in the normal mode of operation. Each of wireless AC power signal 708-1, data-modulated wireless AC signal 708-2, and back telemetry AC signal 710 may be implemented as RF signals having carrier frequencies in the RF band of the electromagnetic spectrum.

As shown, wireless AC power signal 708-1 may have a relatively low frequency and a relatively stable magnitude. As described above, this low frequency and consistency may allow power to be transmitted more efficiently than if power were modulated with data so as to cause the signal to constantly start and stop (e.g., as illustrated for data-modulated wireless AC signal 708-2). While, over a short period of time, wireless AC power signal 708-1 may appear to have a constant, fixed amplitude, it will be understood that the amplitude may vary over time in accordance with the variance of sound intensity in the environment and the resultant DC voltage level provided by sound processor 702 on conductors 502-1 and 502-2, as described above.

In certain implementations, as further illustrated by FIG. 7, data-modulated wireless AC signal 708-2 may be transmitted using a higher carrier frequency than wireless AC power signal 708-1 (e.g., for the reasons described above), Data may be modulated onto the signal in any suitable manner. For example, active headpiece 400 may be configured to wirelessly transmit the data-modulated wireless AC signal 708-2 using an on-off keying ("OOK") modulation technique, as shown. This technique, as illustrated in FIG. 7, may include modulating data bits onto the signal by switching the carrier frequency completely on (e.g., for a '1' data bit) and off (e.g., for a '0' data bit), In other examples, data may be modulated in other ways such as by using an amplitude shift keying ("ASK") modulation technique in which the signal is not switched fully on and off, but rather reduced and increased to two different non-zero levels. Because power is transmitted separately on wireless AC power signal 708-1 in this implementation, data-modulated wireless AC signal 708-2 may have a relatively small amplitude so as to be transmitted as efficiently as possible.

As further shown in FIG. 7, active headpiece 400 may be further configured to wirelessly receive, from cochlear implant 704, back telemetry AC signal 710. For example, back telemetry AC signal 710 may be implemented as an additional data-modulated wireless AC signal (e.g., similar to data-modulated wireless AC signal 708-2) upon which back telemetry data is modulated. In some examples, rather than a data-modulated signal, back-telemetry data may involve more basic feedback such as a simple acknowledge (ACK) or non-acknowledge (HACK) flag. Active headpiece 400 may provide the data received by way of back telemetry AC signal 710 to sound processor 702 in any suitable manner and/or over any conductor as may serve a particular implementation. For instance, the back telemetry data may be transmitted over conductors 502-1 and 502-2, over an additional conductor dedicated to back telemetry data (not explicitly shown), or over any other suitable conductor.

As mentioned above, FIG. 9 shows (along with FIG. 6) another illustrative implementation 900 of an ASIC 504 for use within an implementation of active headpiece 400 (e.g., implementation 500, etc.). Implementation 900 is similar to implementation 600 described above, but includes only one clock control loop configured to generate one synthesized clock signal. This is possible because a single wireless AC transmission facility is used (rather than the separate power and data AC transmission facilities of implementation 600) to wirelessly transmit both AC power and forward telemetry data on a single wireless AC signal at the carrier frequency of the synthesized clock signal.

Figure 9:
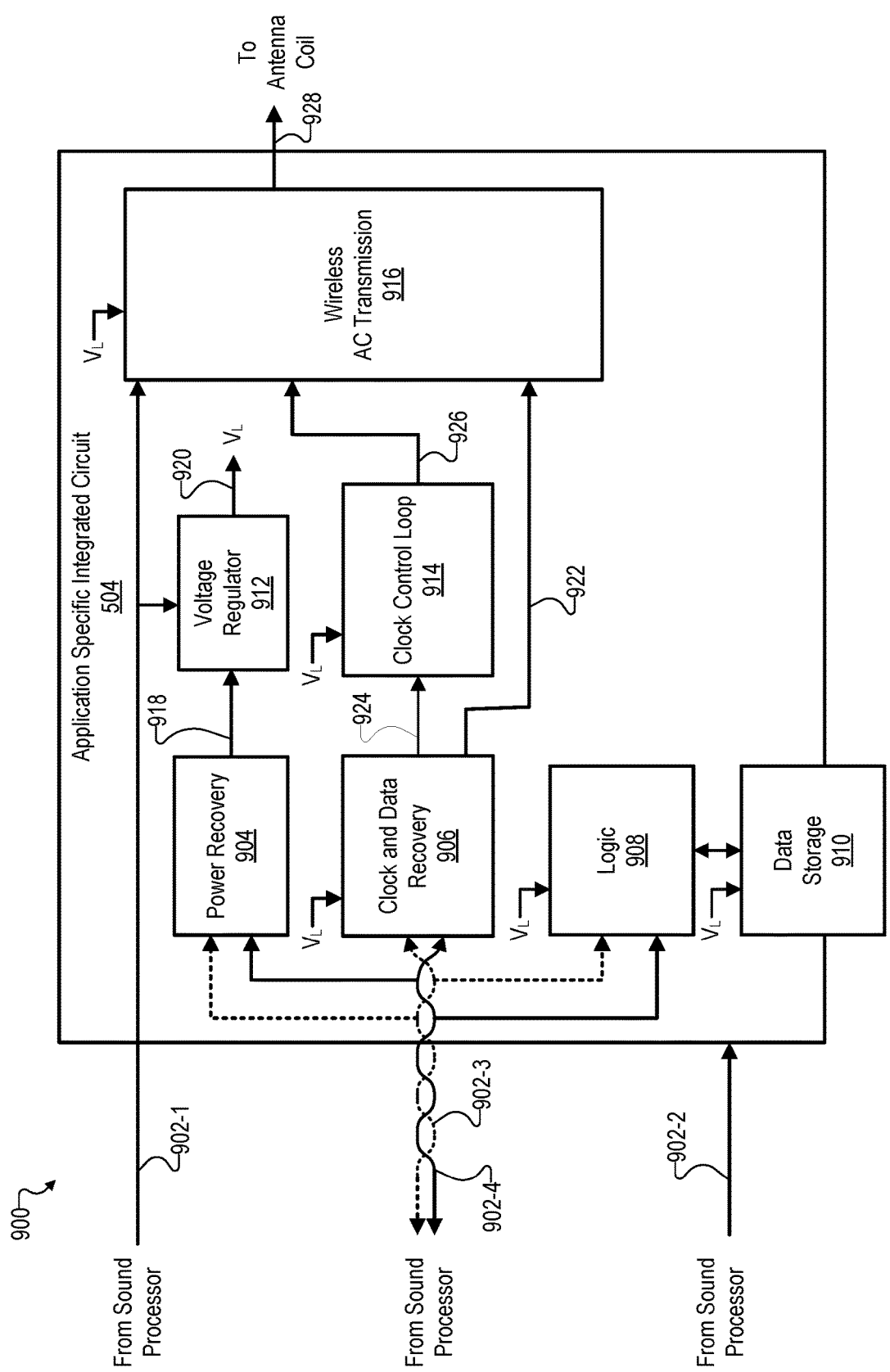
FIG. 9 shows another illustrative implementation of an application specific integrated circuit for use within the active headpiece of FIG. 4 according to principles described herein.

Unless otherwise noted, it will be understood that the components of implementation 900 may be employed to perform a similar or identical function as like-numbered components of implementation 600, described above. For example, as shown in FIG. 9, implementation 900 of ASIC 504 may receive various inputs 902 (e.g., inputs 902-1 through 902-4) that are analogous to inputs 602 and used by a variety of functional blocks including, without limitation, a power recovery facility 904 (analogous to power recovery facility 604), a clock and data recovery facility 906 (analogous to clock and data recovery facility 606), a logic facility 908 (analogous to logic facility 608), a data storage facility 910 (analogous to data storage facility 610), and a voltage regulator 912 (analogous to voltage regulator 612). Rather than two clock control loops, as are included in implementation 600 (clock control loops 614-1 and 614-2), implementation 900 is shown to include a single clock control loop 914 that performs the same function of generating a synthesized clock signal at a particular carrier frequency. Additionally, rather than two wireless AC transmission facilities, as are included in implementation 600 (wireless AC power transmission facility 616-1 and wireless AC data transmission facility 616-2), implementation 900 is shown to include a single wireless AC transmission facility 916. As with implementation 600, it will be understood that implementation 900 may also include any other facilities, components, etc. as may serve a particular implementation.

Similarly as described above with respect to respective components of implementation 600, power recovery facility 904 may generate a recovered power 918, voltage regulator 912 may generate a logic power 920, clock and data recovery facility 906 may recover a data signal 922 and a clock signal 924, and clock control loop 914 may synthesize a clock signal 926. As will be described in more detail below, in implementations in which the power and data are to be wirelessly transmitted on a single signal, it may be desirable for the frequency of synthesized clock signal 926 (i.e., the carrier frequency that will be used to wirelessly transmit the power and data) to be relatively low for power efficiency, emissions, and/or other purposes. For instance, rather than a relatively high frequency of 49.0 MHz mentioned above for the frequency of synthesized clock signal 626-2, the frequency of synthesized clock signal 926 may be 13.56 MHz or another relatively low frequency that may be selected to account for radiated emissions compliance and so forth.

As shown, clock signal 926 may be used by wireless AC transmission facility 916 as a carrier frequency for a transmission output 928 implemented as an RF signal that may carry AC power derived from DC power received by way of input 902-1 and that may be modulated with forward telemetry data derived from recovered data signal 922. As such, clock signal 926 may be implemented to use any clock frequency as may serve as a suitable power carrier frequency and a suitable data carrier frequency in a particular implementation. For instance, as mentioned above, the clock frequency of clock signal 626 may be programmed to a frequency of 13.56 MHz or another suitable frequency upon which emission regulations (e.g., FCC regulations in the United States) allow cochlear implant systems to transmit.

As mentioned above, FIG. 10 shows (along with FIG. 7) another illustrative configuration 1000 in which active headpiece 400 interoperates with a sound processor 1002 and a cochlear implant 1004 within an illustrative cochlear implant system. Configuration 1000 is similar to configuration 700 described above, but includes only one data-modulated AC signal configured to carry both power and forward telemetry data, rather than the separate signals shown in configuration 700.

Figure 10:
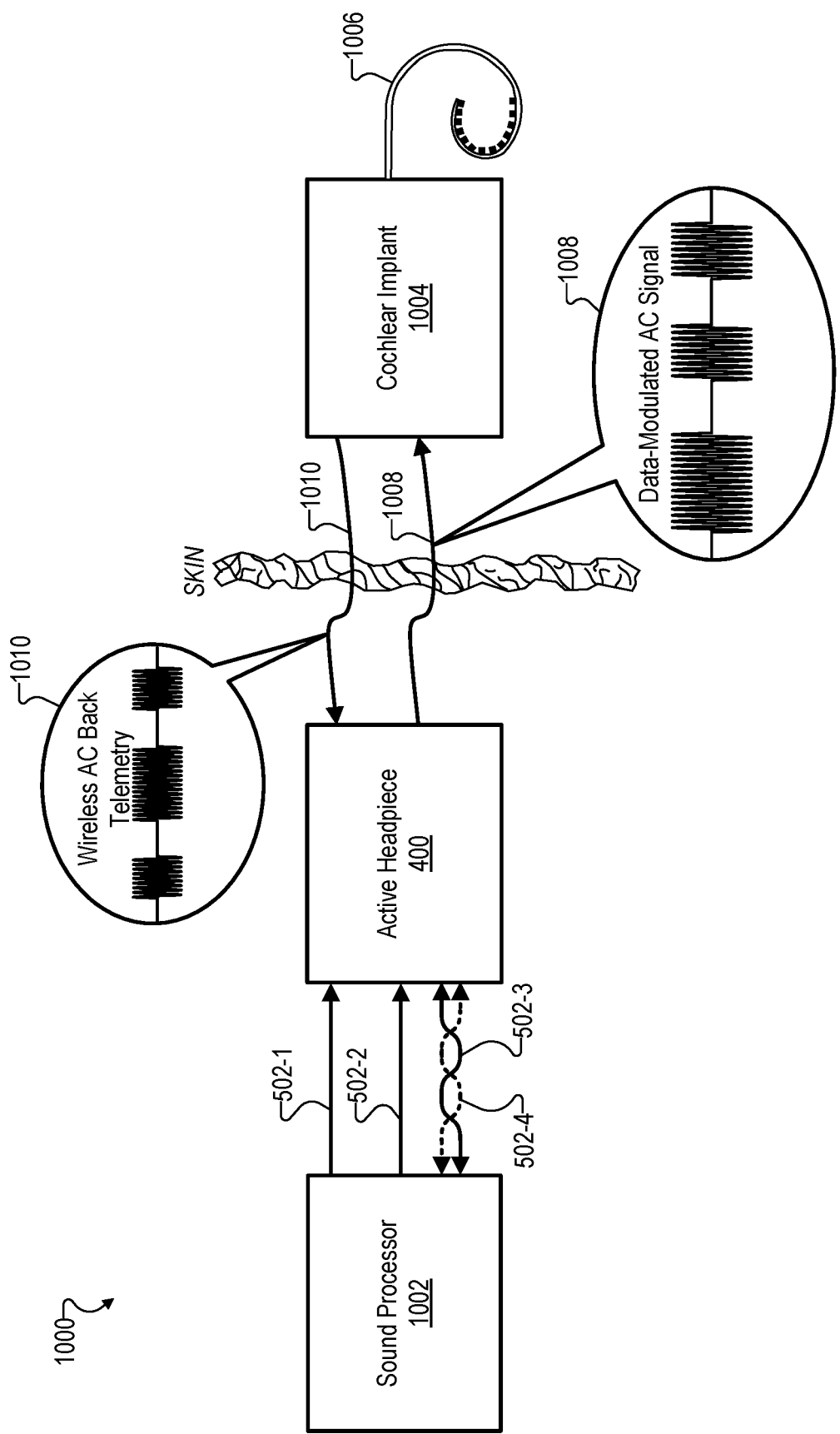
FIG. 10 shows another illustrative configuration in which the active headpiece of FIG. 4 interoperates with a sound processor and a cochlear implant within an illustrative cochlear implant system according to principles described herein.

The cochlear implant system comprising the components of configuration 1000 is analogous to the cochlear implant system of configuration 700 described above in relation to FIG. 7. As such, unless otherwise noted, it will be understood that the components of configuration 1000 may be employed to perform a similar or identical function as like-numbered components of configuration 700. For example, as shown in FIG. 10, sound processor 1002 may communicate, using either or both of the operating modes described above in relation to FIG. 8 or other suitable operating modes, with active headpiece 400 using a 4-conductor interface having signals 502 (e.g., signals 502-1 through 502-4). Additionally, configuration 1000 further illustrates a wireless, transcutaneous interface between active headpiece 400 and a cochlear implant 1004 (analogous to cochlear implant 704) with an electrode lead 1006 (analogous to electrode lead 706) implanted beneath the skin of the recipient. However, instead of separate signals for power and data (e.g., such as wireless AC power signal 708-1 and data-modulated wireless AC signal 708-2 in configuration 700), configuration 1000 includes a single data-modulated AC signal 1008 that is transmitted through the skin from active headpiece 400 to cochlear implant 1004 with both power and forward telemetry data. Additionally, analogous to back telemetry AC signal 710, configuration 1000 shows a back telemetry AC signal 1010 configured to be transmitted through the skin from cochlear implant 1004 back to active headpiece 400.

As in FIG. 7, FIG. 10 shows illustrative waveforms, broken out from each signal in FIG. 10, that show the shape of data-modulated wireless AC signal 1008 and back telemetry AC signal 1010. These signals are both illustrated as data-modulated AC signals that employ an OOK modulation technique. In the case of data-modulated wireless AC signal 1008, however, the OOK modulation technique may cause the power being provided by way of the signal to start and stop in a manner that reduces the efficiency of the system or otherwise limits the amount of power that can be transcutaneously delivered from active headpiece 400 to cochlear implant 1004. Accordingly, in certain examples, data-modulated AC signal 1008 may be modulated using an ASK technique (not explicitly shown) that allows power to continuously be delivered to cochlear implant 1004. More specifically, the electronic circuitry of active headpiece 400 may be configured to wirelessly transmit the AC power and the forward telemetry data by way of data-modulated AC signal 1008 using either an OOK modulation technique or an ASK modulation technique to modulate the forward telemetry data onto the AC power carried at the carrier frequency of the synthesized clock signal.

As has been mentioned, wireless RF signals such as wireless AC power signal 708-1 or data-modulated AC signals 708-2 or 1008 may be generated with various carrier frequencies for various reasons (e.g., bandwidth considerations, emissions compliance, power efficiency, etc.), Different carrier frequencies may have different advantages and drawbacks. Accordingly, systems and methods described herein for wirelessly transmitting power and data to an implantable stimulator may incorporate certain features to take advantage of the advantages of a selected carrier frequency and/or to mitigate challenges associated with a selected carrier frequency.

Figure 11:
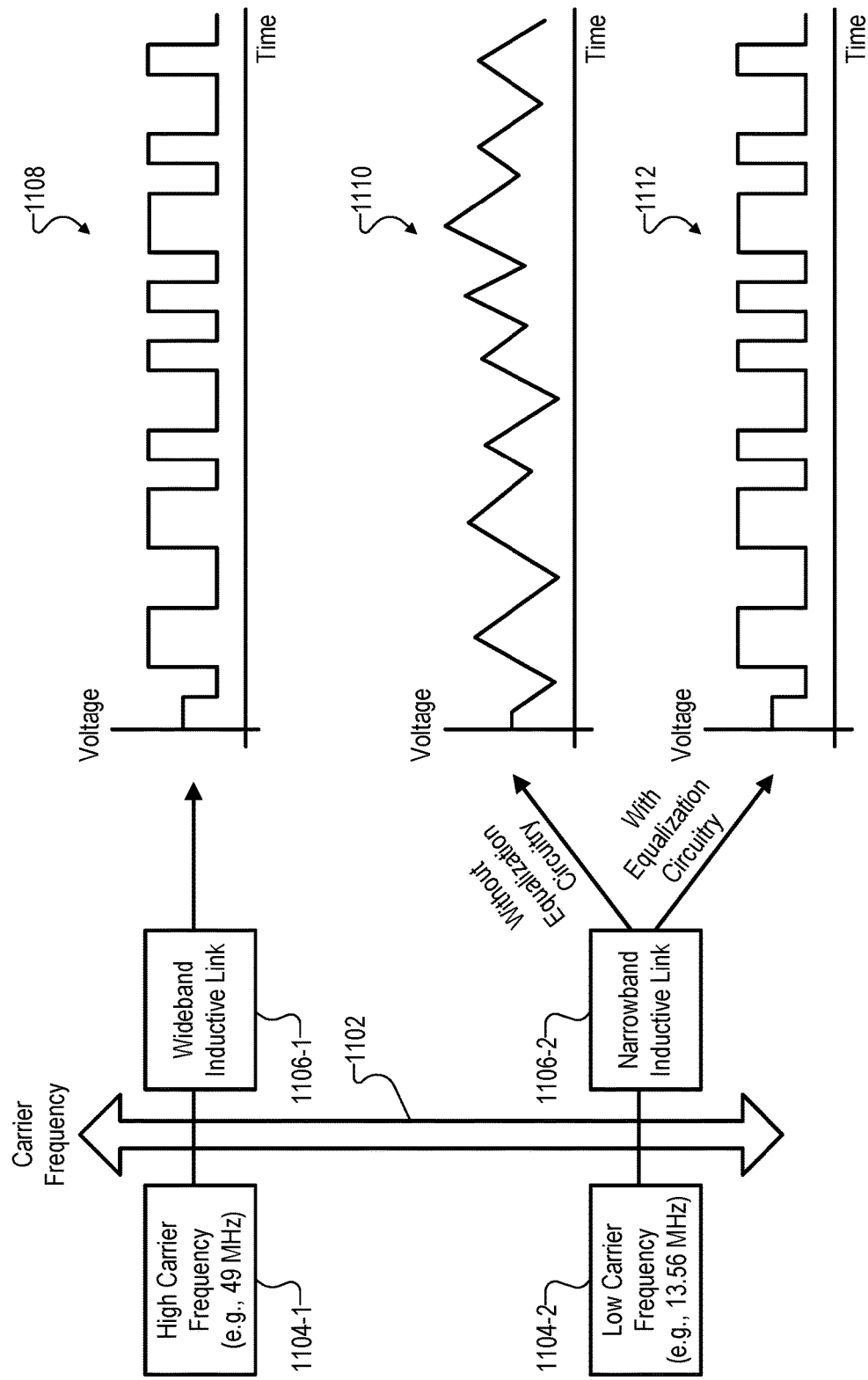
FIG. 11 shows illustrative waveforms representative of wireless signals as received by an implantable stimulator over different inductive links associated with different carrier frequencies and bandwidths according to principles described herein.

To illustrate one example, FIG. 11 shows example waveforms representative of wireless signals as received by an implantable stimulator over different inductive links associated with different carrier frequencies and bandwidths. Specifically, as shown, a spectrum 1102 of different carrier frequencies is illustrated by an arrow that represents relatively high carrier frequencies toward the top of the spectrum and relatively low carrier frequencies toward the bottom of the spectrum. On spectrum 1102, two specific carrier frequencies 1104 (i.e., high carrier frequency 1104-1 and low carrier frequency 1104-2) are called out as particular examples. Specifically, high carrier frequency 1104-1 (e.g., a frequency such as 49.0 MHz) is shown to be placed relatively high on spectrum 1102, while low carrier frequency 1104-2 (e.g., a frequency such as 13.56 MHz) is shown to be placed relatively low on spectrum 1102.

One consequence of the carrier frequency 1104 selected for a particular implementation is the effect that the carrier frequency 1104 has on the bandwidth afforded to data transmitted using the selected carrier frequency. For example, a relatively low carrier frequency (e.g., low carrier frequency 1104-2) may provide a narrower bandwidth than a relatively high carrier frequency (e.g., high carrier frequency 1104-1). To illustrate, FIG. 11 shows different bandwidth inductive links 1106 (e.g., inductive links 1106-1 and 1106-2) to be associated with each of carrier frequencies 1104. Specifically, high carrier frequency 1104-1 is shown to be associated with a wideband inductive link 1106-1 (i.e., an inductive link with a relatively wide bandwidth that facilitates the transmission of relatively high-speed data rates and relatively fast data edges), while low carrier frequency 1104-2 is shown to be associated with a narrowband inductive link 1106-2 (i.e., an inductive link with a relatively narrow bandwidth that would make it more difficult to transmit high-speed data rates and relatively fast data edges).

Different waveforms 1108-1112 each show voltage along the y-axis and time along the x-axis to illustrate aspects of how an example data signal might be received when transmitted over the different inductive links 1106, Specifically, a waveform 1108 shows that the data signal transmitted over wideband inductive link 1106-1 has fast (i.e., highly vertical) edges that are desirable for a digital signal like this data signal. It will be understood that a real physical signal may never look as ideal (e.g., with as square of edges, etc.) as depicted in waveform 1108, but the principle illustrated by FIG. 11 is that a relatively optimally-shaped digital signal may be readily transmitted over a wideband inductive link such as wideband inductive link 1106-1. In contrast, a waveform 1110 shows that the data signal transmitted over narrowband inductive link 1106-2 may have slow (i.e., not very vertical) edges that are undesirable for a digital signal. Accordingly, in examples where a low carrier frequency such as carrier frequency 1104-2 is selected (e.g., for efficiency, emissions compliance, or other purposes) and a narrowband inductive link such as inductive link 1106-2 is used, equalization circuitry may be employed to help compensate for distortion (e.g., slow edges, etc.) introduced onto the digital signal as a result of the narrow bandwidth of the inductive link. Specifically, as shown, while a non-ideal waveform such as waveform 1110 may result from using narrowband inductive link 1106-2 in implementations that do not employ equalization circuitry ("Without Equalization Circuitry"), a more optimal waveform such as a waveform 1112 (which, as shown, may be similarly or identically optimal as waveform 1108 described above) may result from using narrowband inductive link 1106-2 in implementations that do employ equalization circuitry ("With Equalization Circuitry").

Accordingly, in certain implementations, a carrier frequency of a synthesized clock signal may be relatively low (e.g., less than 49 MHz, less than 20 MHz, less than 15 MHz, approximately 13.56 MHz or another suitable low frequency, etc.), and a communication link over which AC power and forward telemetry data is wirelessly transmitted to an implantable stimulator may be a transcutaneous narrowband inductive link (e.g., narrowband inductive link 1106-2). In these implementations, the wireless transmitting of the forward telemetry data may be performed by wirelessly transmitting, at the relatively low carrier frequency, a forward telemetry signal onto which the forward telemetry data is modulated. Electronic circuitry implemented in these implementations may include equalization circuitry configured to facilitate recovery, by the implantable stimulator, of the forward telemetry data from the forward telemetry signal by compensating for distortion introduced onto the forward telemetry signal as a result of bandwidth limitations imposed by the transcutaneous narrowband inductive link. For example, the equalization circuitry may allow the implantable stimulator to derive a data signal such as illustrated by waveform 1112 from the forward telemetry signal rather than a data signal such as illustrated by waveform 1110.

In implementations where it is used, equalization circuitry may be deployed in different ways by system 100 (e.g., an active headpiece), by implantable stimulator 102 (e.g., a cochlear implant), or by both of these components. To illustrate, FIGS. 12A-12C show illustrative configurations for how equalization circuitry may be implemented within a transcutaneous transmission system such as system 100 and/or an implantable stimulator such as implantable stimulator 102 to compensate for distortion on wireless signals exchanged between the transcutaneous transmission system and the implantable stimulator.

Figure 12A:
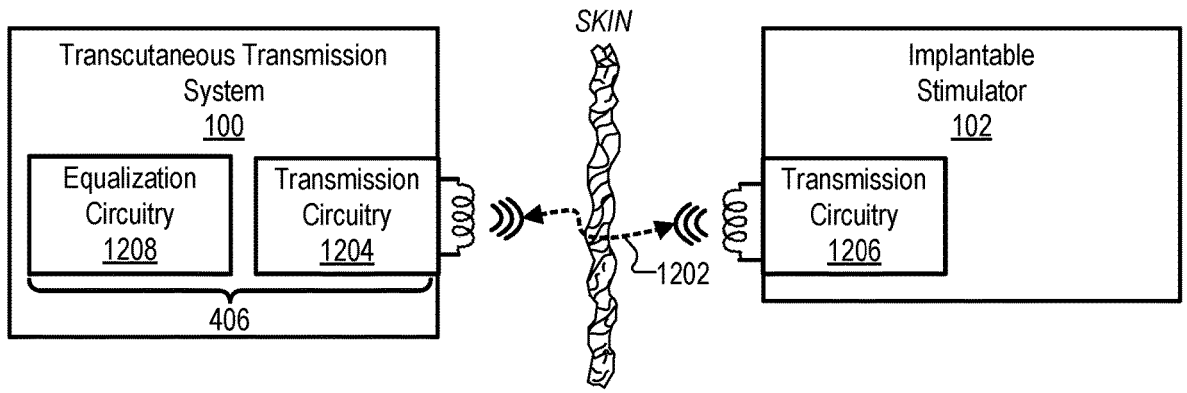
FIGS. 12A-12C show illustrative configurations for how equalization circuitry may be implemented within a transcutaneous transmission system and/or an implantable stimulator to compensate for distortion according to principles described herein.
Figure 12B:
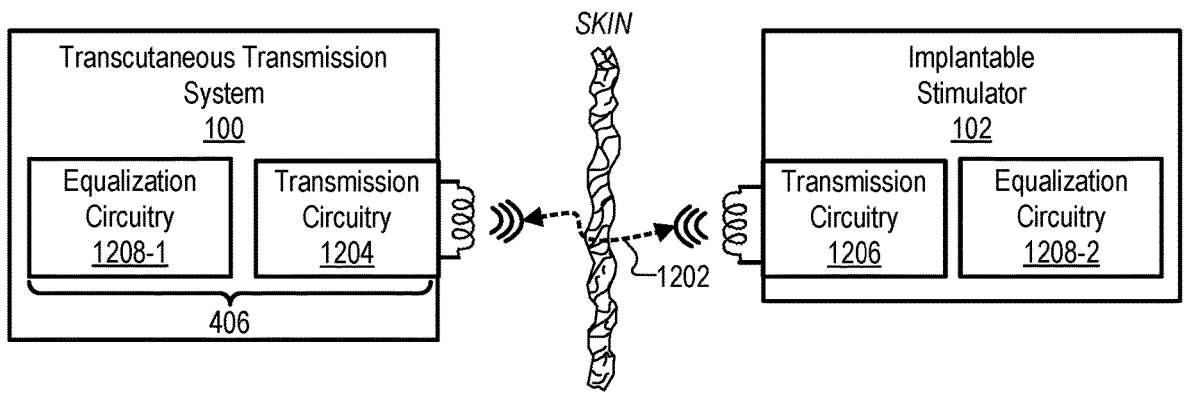
Figure 12C:
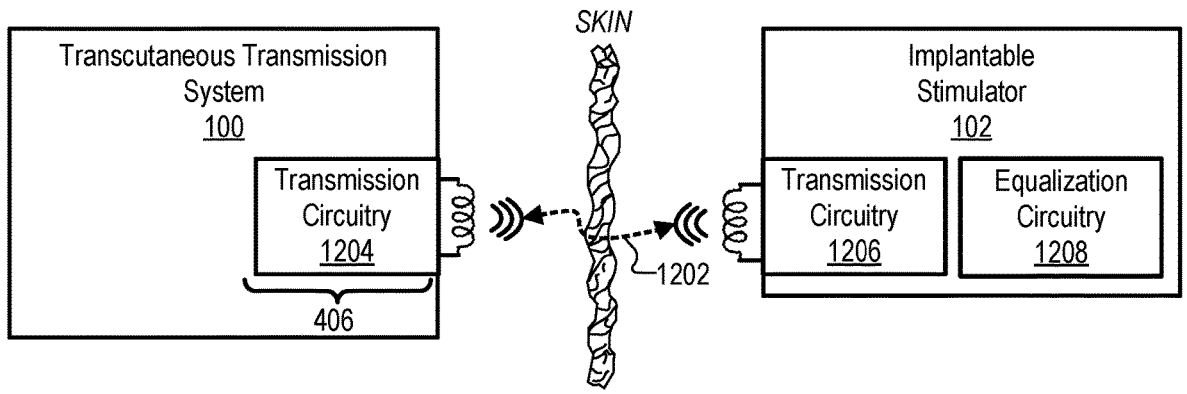

In each of FIGS. 12A-12C, an implementation of system 100 and an implementation of implantable stimulator 102 are shown to be separated by a layer of skin of a recipient, indicating that the implantable stimulator is implanted within the recipient and communicating with the transcutaneous transmission system as the system is external from the recipient's body. At least one wireless (e.g., RF) signal 1202 is shown to be transmitted between system 100 and implantable stimulator 102 in each of the figures. This signal will be understood to represent any of a AC power signal provided by system 100 to implantable stimulator 102, a forward telemetry data signal provided by system 100 to implantable stimulator 102, a combination AC signal that carries both power and data from system 100 to implantable stimulator 102 in any of the ways described herein, a backward telemetry data signal provided by implantable stimulator 102 to system 100, or any other suitable signal or signals that may be communicated between system 100 and implantable stimulator 102 in a particular implementation.

As shown, transmission circuitry 1204 in system 100 and transmission circuitry 1206 in implantable stimulator 102 is used to facilitate the exchange of wireless signal 1202, such as by preparing and inductively transmitting wireless signal 1202, receiving and processing wireless signal 1202, and so forth. Additionally, equalization circuitry 1208 is shown to be included within system 100 and/or within implantable stimulator 102 to pre-compensate, post-compensate, or otherwise compensate for distortion introduced onto wireless signal 1202 as a result of bandwidth limitations imposed by a transcutaneous narrowband link between system 100 and implantable stimulator 102. For example, equalization circuitry 1208 may include passive or active components configured to compensate for the distortion by forming, shaping, processing, and/or otherwise altering the signal to ensure that the signal finally received looks similar to the example of waveform 1112 and dissimilar to the example of waveform 1110.

As illustrated specifically in FIG. 12A, in certain examples, equalization circuitry 1208 may be included within electronic circuitry 406 of system 100 together with transmission circuitry 1204. In this example, equalization operations for forward telemetry signals would be limited to pre-compensation of the distortion, and implantable stimulator 102 is shown to not include any equalization circuitry. For instance, a forward telemetry signal may be pre-distorted in a manner that will be undone by the distortion of the narrowband link so that implantable stimulator 102 will receive a non-distorted signal. Conversely, a backward telemetry signal in this example would need to be undistorted upon receipt by system 100.

As illustrated specifically in FIG. 12B, equalization circuitry 1208 may, in other examples, be included both within electronic circuitry 406 of system 100 (equalization circuitry 1208-1) and within implantable stimulator 102 together with transmission circuitry 1206 (equalization circuitry 1208-2). In this example, equalization operations may be performed both on the transmission side and on the receiving side of the narrowband link such that some pre-distortion may be included on the signal before transmission (which may be partially corrected by the distortion of the narrowband link) and some post-distortion is performed on the signal after being received. Additionally or alternatively, by including equalization circuitry 1208 on both sides of a transcutaneous narrowband link, wireless signals being transmitted over the link in both directions (e.g., forward telemetry signals and backward telemetry signals) may be treated the same way (e.g., both pre-compensated, both post-compensated, both treated with a combination of pre-compensation and post-compensation, etc.).

As illustrated specifically in FIG. 12C, equalization circuitry 1208 may, in still other examples, be included only on the side of implantable stimulator 102 with transmission circuitry 1206. In this example, forward telemetry equalization operations would be limited to post-compensation of the signal distortion since system 100 does not include any equalization circuitry for pre-distorting the signal. In this example, backward telemetry equalization would be limited to pre-compensation by implantable stimulator 102.

Figure 13:
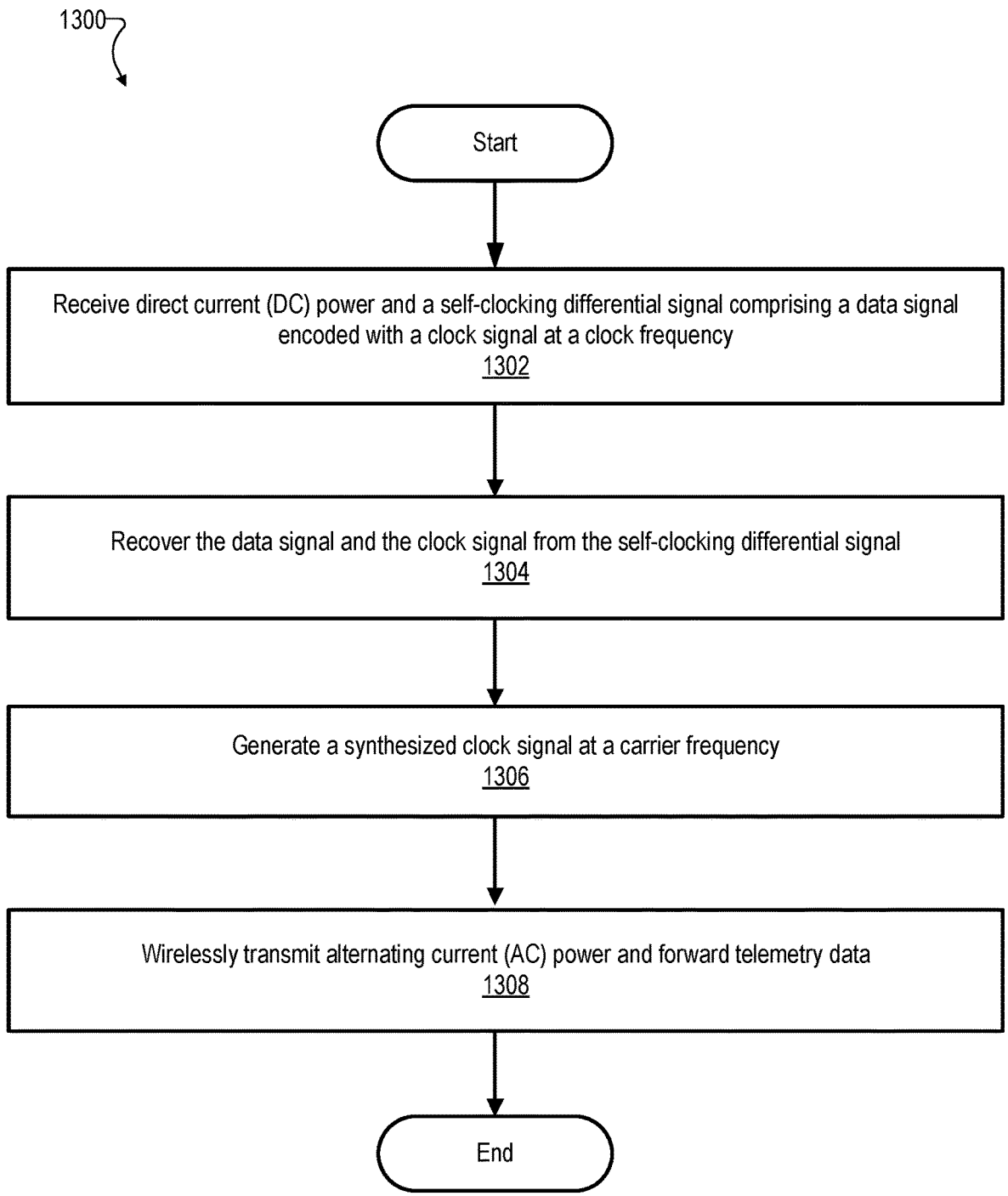
FIG. 13 shows an illustrative method for wirelessly transmitting power and data to an implantable stimulator according to principles described herein.

FIG. 13 shows an illustrative method 1300 for wirelessly transmitting power and data to an implantable stimulator in accordance with principles described herein. While FIG. 13 illustrates exemplary operations according to one embodiment, other embodiments may omit, add to, reorder, and/or modify any of the operations shown in FIG. 13. In some examples, some or all of the operations shown in FIG. 13 may be performed by a transcutaneous transmission system such as system 100, or any implementation thereof that is described herein (e.g., an active headpiece such as active headpiece 400) or that may serve a particular embodiment.

In operation 1302, a transcutaneous transmission system included within an implantable stimulation system (e.g., a cochlear implant system, etc.) associated with a recipient may receive DC power and a self-clocking differential signal. For example, the transmission system may receive the DC power and the self-clocking differential signal from an external device housed separately from the transmission system (e.g., a sound processor in the example of the cochlear implant system). The self-clocking differential signal may comprise a data signal encoded with a clock signal at a clock frequency. The data signal may be representative of data configured for use by an implantable stimulator implanted within the recipient (e.g., a cochlear implant in the cochlear implant system example). Operation 1302 may be performed in any of the ways described herein.

In operation 1304, the transcutaneous transmission system may recover the data signal and the clock signal from the self-clocking differential signal received in operation 1302. Specifically, the transmission system may recover the clock signal at the clock frequency. Operation 1304 may be performed in any of the ways described herein.

In operation 1306, the transcutaneous transmission system may generate a synthesized clock signal at a carrier frequency. For example, the transmission system may generate the synthesized clock signal based on the clock signal at the clock frequency that was recovered in operation 1304. Operation 1306 may be performed in any of the ways described herein.

In operation 1308, the transcutaneous transmission system may use the synthesized dock signal generated in operation 1306 to wirelessly transmit AC power and forward telemetry data to the implantable stimulator implanted within the recipient. For example, the AC power may be based on the DC power received at operation 1302 and the forward telemetry data may be based on the data signal recovered at operation 1304. Operation 1308 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A system comprising:
electronic circuitry configured to:
  receive a self-clocking differential signal comprising a data signal encoded with a clock signal at a clock frequency;
  recover, from the self-docking differential signal, the data signal and the clock signal; and
  wirelessly transmit, based on the recovered dock signal and to an implantable stimulator implanted within a recipient, a forward telemetry signal representing data recovered from the data signal.

2. The system of claim 1, wherein:
the electronic circuitry is further configured to generate, based on the recovered dock signal, a synthesized dock signal at a carrier frequency; and
the wireless transmitting of the forward telemetry signal includes modulating the data recovered from the data signal onto a carrier signal generated at the carrier frequency using the synthesized clock signal.

3. The system of claim 1, wherein:
the electronic circuitry is further configured to:
receive direct current (DC) power; and
based on the DC power, wirelessly transmit alternating current (AC) power to the implantable stimulator to power the implantable stimulator; and
the wireless transmitting of the forward telemetry signal includes modulating the data recovered from the data signal onto the AC power.

4. The system of claim 1, wherein:
the wireless transmitting of the forward telemetry signal includes wirelessly transmitting a data-modulated alternating current (AC) signal that modulates the data recovered from the data signal onto AC power carried at a carrier frequency of a synthesized dock signal derived from the recovered dock signal; and
the carrier frequency is different from the dock frequency of the recovered clock signal.

5. The system of claim 4, wherein the data-modulated AC signal modulates the data recovered from the data signal onto the AC power carried at the carrier frequency using an on-off keying (OOK) modulation technique.

6. The system of claim 4, wherein the data-modulated AC signal modulates the data recovered from the data signal onto the AC power carried at the carrier frequency using an amplitude shift keying (ASK) modulation technique.

7. The system of claim 1, wherein:
the electronic circuitry is further configured to generate, based on the recovered clock signal, a first synthesized clock signal at a first carrier frequency and a second synthesized clock signal at a second carrier frequency that is at least twice as high as the first carrier frequency; and
the wireless transmitting of the forward telemetry signal includes:
wirelessly transmitting, using the first synthesized clock signal, a first alternating current (AC) signal that carries AC power at the first carrier frequency, and
wirelessly transmitting, using the second synthesized clock signal, a second AC signal onto which the data recovered from the data signal is modulated, the second AC signal transmitted at the second carrier frequency.

8. The system of claim 1, further comprising a single antenna coil;
wherein:
the electronic circuitry is further configured to generate, based on the recovered clock signal, a first synthesized clock signal at a first carrier frequency and a second synthesized clock signal at a second carrier frequency; and
the wireless transmitting of the forward telemetry signal includes:
wirelessly transmitting, using the first synthesized clock signal and by way of the single antenna coil, a first alternating current (AC) signal that carries AC power to the implantable stimulator at the first carrier frequency, and
wirelessly transmitting, using the second synthesized clock signal and further by way of the single antenna coil, a second AC signal onto which the data recovered from the data signal is modulated, the second AC signal transmitted at the second carrier frequency.

9. The system of claim 1, further comprising:
a first antenna coil; and
a second antenna coil distinct from the first antenna coil;
wherein:
the electronic circuitry is further configured to generate, based on the recovered clock signal, a first synthesized clock signal at a first carrier frequency and a second synthesized clock signal at a second carrier frequency; and
the wireless transmitting of the forward telemetry signal includes:
wirelessly transmitting, using the first synthesized clock signal and by way of the first antenna coil, a first alternating current (AC) signal that carries AC power to the implantable stimulator at the first carrier frequency, and
wirelessly transmitting, using the second synthesized clock signal and by way of the second antenna coil, a second AC signal onto which the data recovered from the data signal is modulated, the second AC signal transmitted at the second carrier frequency.

10. The system of claim 1, wherein:
the wireless transmitting of the forward telemetry signal includes wirelessly transmitting, over a communication link, a data-modulated alternating current (AC) signal that modulates the data recovered from the data signal onto AC power carried at a carrier frequency of a synthesized clock signal;
the synthesized clock signal is derived from the recovered clock signal and the carrier frequency is less than 49 MHz;
the communication link is a transcutaneous narrowband inductive link; and
the electronic circuitry includes equalization circuitry configured to facilitate recovery, by the implantable stimulator implanted within the recipient, of the data modulated onto the data-modulated AC signal by compensating for distortion introduced onto the forward telemetry signal as a result of bandwidth limitations imposed by the transcutaneous narrowband inductive link.

11. The system of claim 1, further comprising a housing within which the electronic circuitry is disposed;
wherein:
the electronic circuitry includes an interface that is communicatively coupled, by way of a cable, to a sound processor external to the recipient and to the housing; and
the interface is configured to receive the self-clocking differential signal from the sound processor by way of the cable.

12. The system of claim 1, implemented as a headpiece included within a cochlear implant system associated with the recipient, wherein:
the implantable stimulator is implemented as a cochlear implant included within the cochlear implant system;
the data signal is representative of data configured for use by the cochlear implant; and
the electronic circuitry is configured to wirelessly transmit the forward telemetry signal transcutaneously to the cochlear implant while the cochlear implant is implanted within the recipient.

13. The system of claim 1, wherein the system is configured to operate in one mode of operation at a time from a plurality of supported modes of operation including:
a normal mode of operation in which:
the electronic circuitry receives direct current (DC) power by way of a first conductor within a cable and receives the self-clocking differential signal by way of a second conductor and a third conductor within the cable, and
the electronic circuitry performs the recovering of the data and clock signals and the wireless transmitting of the forward telemetry signal; and
a setup mode of operation in which:
the electronic circuitry receives DC power by way of the first conductor, receives a setup data signal by way of the second conductor, and receives a setup clock signal by way of the third conductor, and
rather than performing the recovering of the data and clock signals and the wireless transmitting of the forward telemetry signal, the electronic circuitry performs one or more system setup operations based on the setup data signal and the setup clock signal;
wherein:
the one or more system setup operations performed by the electronic circuitry in the setup mode of operation include register configuration operations to set up a dock control loop circuit used to derive a carrier frequency from the clock signal, and
the forward telemetry signal is wirelessly transmitted at the carrier frequency derived using the clock control loop circuit.

14. The system of claim 1, further comprising:
a housing within which the electronic circuitry is disposed; and
a microphone communicatively coupled, by way of a cable, to a sound processor external to the recipient and to the housing;
wherein:
the microphone is configured to detect sound presented to the recipient and to generate and provide, to the sound processor, a signal representative of the sound, and
the data signal is generated by the sound processor based on the signal representative of the sound.

15. The system of claim 1, wherein the electronic circuitry is further configured to:
receive direct current (DC) power;
access a fixed DC power having a voltage that is fixed at a particular level by deriving the fixed DC power from the received DC power or by recovering the fixed DC power from the self-clocking differential signal; and
use the fixed DC power to perform the recovering of the data signal and the clock signal.

16. The system of claim 1, wherein:
the data signal is encoded with the clock signal at the clock frequency using a zero direct current (DC) balance clock encoding technique; and
the electronic circuitry is configured to recover the data signal and the clock signal in accordance with the zero DC balance clock encoding technique.

17. The system of claim 1, implemented as a headpiece included within a cochlear implant system, the headpiece configured to be powered exclusively by power received from a sound processor included within the cochlear implant system such that no battery is disposed within the headpiece.

18. The system of claim 1, wherein the electronic circuitry is further configured to wirelessly receive backward telemetry data from the implantable stimulator to which the electronic circuitry wirelessly transmits the forward telemetry signal.

19. An application-specific integrated circuit (ASIC) configured to:
receive a self-clocking differential signal comprising a data signal encoded with a clock signal at a clock frequency;
recover, from the self-clocking differential signal, the data signal and the clock signal; and
wirelessly transmit, based on the recovered clock signal and to an implantable stimulator implanted within a recipient, a forward telemetry signal representing data recovered from the data signal.

20. A method comprising:
receiving a self-clocking differential signal comprising a data signal encoded with a clock signal at a clock frequency;
recovering, from the self-clocking differential signal, the data signal and the clock signal; and
wirelessly transmitting, based on the recovered clock signal and to an implantable stimulator implanted within a recipient, a forward telemetry signal representing data recovered from the data signal.

* * * * *